US008092398B2

(12) United States Patent
Weinberg et al.

(10) Patent No.: US 8,092,398 B2
(45) Date of Patent: Jan. 10, 2012

(54) MULTI-AXIS TILT ESTIMATION AND FALL REMEDIATION

(75) Inventors: Marc S. Weinberg, Needham, MA (US); Conrad Wall, III, Boston, MA (US); Kathleen H. Sienko, Cambridge, MA (US); Edward W. O'Neil, Concord, MA (US)

(73) Assignees: Massachusetts Eye & Ear Infirmary, Boston, MA (US); Charles Stark Draper Laboratory, Cambridge, MA (US)

( * ) Notice: Subject to any disclaimer, the term of this patent is extended or adjusted under 35 U.S.C. 154(b) by 1133 days.

(21) Appl. No.: 11/401,106

(22) Filed: Apr. 10, 2006

(65) Prior Publication Data

US 2007/0038268 A1 Feb. 15, 2007

Related U.S. Application Data

(60) Provisional application No. 60/706,538, filed on Aug. 9, 2005.

(51) Int. Cl.

| | |
|---|---|
| ***A61B 5/117*** | (2006.01) |
| ***A61B 5/103*** | (2006.01) |
| ***G01C 9/00*** | (2006.01) |
| ***G01C 17/00*** | (2006.01) |
| ***G01C 19/00*** | (2006.01) |

(52) U.S. Cl. ........................................ 600/595; 702/150

(58) Field of Classification Search .................. 600/587, 600/595; 128/897; 2/465, 455, DIG. 3; 340/573.1; 607/62, 48, 49; 73/865.4, 509, 510; 708/809, 708/811; 702/150
See application file for complete search history.

(56) References Cited

U.S. PATENT DOCUMENTS

| | | | | |
|---|---|---|---|---|
| 3,660,648 | A * | 5/1972 | Kuipers | 708/811 |
| 5,807,284 | A * | 9/1998 | Foxlin | 600/595 |
| 6,162,191 | A * | 12/2000 | Foxlin | 600/595 |
| 6,546,291 | B2 | 4/2003 | Merfeld et al. | |
| 7,150,048 | B2 * | 12/2006 | Buckman | 2/465 |
| 2005/0267549 | A1 | 12/2005 | Della Santina et al. | |
| 2007/0032748 | A1 * | 2/2007 | McNeil et al. | 600/595 |

OTHER PUBLICATIONS

Foxlin, Eric, Inertial Head-Tracker Sensor Fusion by a Complementary Separate-Bias Kalman Filter, Proceedings of VRAIS, 1996.*
www.theage.com.au/articles/2004/1011/1097406475460.html High-tech SOS shirt for the elderly, Oct. 11, 2004.
http://blog.tmcnet.com/glog/tom-keating/gadgets/personal-airbag.asp "VoIP & Gadgets Blog," Mar. 23, 2005.
http://www.theregister.co.uk/2005/03/23/ivoice_airbag_patent/print.html "iVoice files patent on bounding grannies," Mar. 23, 2005.
http://www.hipsaver.ca/news.cfm "HipSaver Hip Protectors achieve 93% compliance," Sep. 2003.

(Continued)

*Primary Examiner* — Brian Szmal
(74) *Attorney, Agent, or Firm* — Fish & Richardson P.C.

(57) ABSTRACT

Among other things, a vestibular prosthesis includes a wearable motion sensing system, the motion sensing system generating a motion signal indicative of a motion thereof, wherein the motion includes rotation about two distinct axes; a signal processor in communication with the motion sensing system, the signal processor being configured to generate an estimate of a tilt of the motion sensing system; and an actuator responsive to the estimate of the tilt made by the signal processor.

28 Claims, 11 Drawing Sheets

OTHER PUBLICATIONS

Kato et al., "Plasma matrix metalloproteinase-8 concentrations are associated with the presence and severity of coronary artery disease," www.pubmed.gov Cic J. , Sep. 2005.

Kentala et al., "Reduction of Postural Sway by Use of a Vibrotactile Balance Prothesis Prototype in Subjects with Vestibular Deficits," Ann Otol Rhinol. Laryngol, p. 404-409112:2003.

Wilson et. al., Matrix metalloproteinase 8 (neutrophil collagenase) in the pathogenesis of abdominal aortic aneurysm. www.pubmed.gov Br J Surg. Jul. 2005, 92(7): 828-33.

Notification Concerning Transmittal of International Preliminary Report on Patentability for International Application No. PCT/US2006/031077 dated Mar. 26, 2009.

* cited by examiner

MULTI-AXIS TILT ESTIMATION AND FALL REMEDIATION

CROSS REFERENCE TO RELATED APPLICATION

This application claims the benefit of the filing date of U.S. Provisional Application No. 60/706,538, which was filed on Aug. 9, 2005, the contents of which are hereby incorporated by reference to this description.

TECHNICAL FIELD

This invention relates to determining the physical orientation of a person, and more particularly to balance prostheses for improving postural stability.

BACKGROUND

The inner ear's vestibular system provides cues about self-motion that help stabilize vision during movement. These cues also enable us to orient ourselves with respect to our surroundings, which helps us to stand and walk. Each inner ear can sense, in 3-D, angular motion and the sum of forces due to linear acceleration and gravity (V. Wilson, B. Peterson, et al., *"Analysis of vestibulocollic reflexes by sinusoidal polarization of vestibular afferent fibers," Journal of Neurophysiology*, Vol. 42, No. 2, 1979, p. 331-46). The central nervous system can process these motion cues to estimate self motion in 6 degrees of freedom: three angular and three linear. When a malfunction occurs in the inner ear, the neural pathways that connect the inner ear to the central nervous system, or the part of the central nervous system that processes self-motion information, due to injury, disease, or to prolonged exposure to altered gravity, motion cues are lost or distorted. This lack of accurate sensory information can result in dizziness, blurred vision, inability to orient correctly (including the ability to align with the vertical), and reduced ability to stand or walk, especially under difficult conditions.

Vestibular or balance prostheses have been developed in the hope of improving postural stability in the balance impaired. Basic uses for balance prostheses include: (1) a vestibular "pacemaker" to reduce dizziness and imbalance due to abnormal fluctuations in the peripheral vestibular system, (2) permanent replacement of vestibular function, (3) temporary replacement of motion cues that commonly occur following ablative surgery of the inner ear, and (4) vestibular/balance rehabilitation.

Balance prostheses may be implantable or non-implantable. An implantable prosthesis delivers self-motion cues to the central nervous system via implanted stimulators. Non-implantable prostheses are a less invasive means of providing some self-motion cues. Such prostheses operate by, for example, stimulating the vestibular nerve via surface electrodes or by displaying self-motion cues using "sensory substitution" (e.g., acoustic inputs or electric currents applied to the tongue). (See P. Bach-y-Rita, "Late post-acute neurologic rehabilitation: neuroscience, engineering and clinical programs," *Arch Phys. Med. Rehab*, Vol. 84, No. 8, 2003, p. 1100-8. and P. Bach-y-Rita, K. A. Kaczmarek, et al., *"Form perception with a 49-point electrotactile stimulus array on the tongue: a technical note," J Rehabil Res Dev*, Vol. 35, No. 4, 1998, p. 427-30.) Stimulation using auditory cues is described in U.S. Pat. No. 5,919,149 ("the '149 patent"), the full disclosure of which is incorporated by reference herein.

U.S. Pat. No. 6,546,291, the full disclosure of which is incorporated herein by reference, describes vestibular prostheses that include tactile vibrators (tactors) mounted on the subject's torso. Several generations of this type of prosthesis have been tested and have reduced sway in vestibulopathic subjects. Initial, single axis tests were performed, with the subject receiving only information about forward (or sideward) motion. A particularly noteworthy result was the ability of vestibulopathic subjects deprived of visual and proprioceptive inputs to stand without falling. (M. S. Weinberg and C. Wall, *"MEMS Inertial Sensor Assembly for Vestibular Prosthesis," The Institute of Navigation 59th Annual Meeting*, Albuquerque, N. Mex., Jun. 23-25, 2002; M Weinberg and C. Wall, *"Sensor Assembly for Postural Control Balance Prosthesis," Transducers '03*, Boston, Mass., Jun. 9-12; J. Vivas, *"A Precursor to a Balance Prosthesis via Vibrotactile Display," Mass. Institute of Technology Masters Thesis*, May, 2001; D. Merfeld, S. Rauch, et al., *Vestibular Prosthesis Based on Micromechanical Sensors*, U.S. Pat. No. 6,546,291, Apr. 8, 2003; and E. Kentala, J. Vivas, and C. Wall III, *"Reduced Postural Sway by use of a Vibrotactile Balance Prosthesis," Ann Otol Rhinol Laryngol*, Vol. 5, No. 112, 2003.)

SUMMARY

The present disclosure describes vestibular prostheses that are capable of providing a subject with information concerning tilt and sway in multiple axes; and detecting and remediating falls using such prostheses. The prostheses utilize estimates, discussed below, which detect tilt with respect to gravity and angular rotation. The estimates are accurate over large angle operation and over long periods of time. The estimates reduce the impact of gyroscopic bias errors (which could integrate to large angular errors) and lateral accelerations (which could introduce incorrect phase to the control loops).

In general, in one aspect, a vestibular prosthesis includes a wearable motion sensing system, the motion sensing system generating a motion signal indicative of a motion thereof, the motion thereof including rotation about two distinct axes; a signal processor in communication with the motion sensing system, the signal processor being configured to generate an estimate of a tilt of the motion sensing system; and an actuator responsive to the estimate of the tilt made by the signal processor.

Implementations may include one or more of the following features. The motion sensor includes a stimulator in communication with the actuator, the stimulator being configured to generate a stimulus signal based on the tilt of the motion sensing system. The motion sensing system includes accelerometers and gyroscopes. The signal processor is configured to generate a first estimate of the tilt based on output from the accelerometers, and to generate a second estimate of the tilt based on output from the gyroscopes. The signal processor is configured to generate a third estimate of the tilt based on the first estimate and the second estimate. The signal processor is configured to represent the first, second, and third estimates as quaternions. The signal processor is configured to generate: the first estimate based on Euler angles relating a motion of the accelerometers to the tilt of the motion sensing system; and the second estimate based on Euler angles relating motion of the gyroscopes to the tilt of the motion sensing system. The signal processor is configured to determine a first redundant Euler angle and a second redundant Euler angle, and generate the first estimate based further on the first redundant Euler angle, and generate the second estimate based on the second redundant Euler angle. The signal processor is configured to generate the third estimate by using a Kalman filter. The motion sensing system includes an airbag in communication with the actuator, and the signal processor is configured to cause the actuator to deploy the airbag when the tilt of the motion sensing system is within a pre-determined range, or when the motion has pre-determined characteristics.

In general, in another aspect, estimating a tilt of a wearer includes generating a motion signal indicative of rotations about at least two axes as experienced by the wearer; and processing the motion signal to generate an estimate of the tilt of the wearer.

Implementations may include one or more of the following features. Estimating tilt includes providing an output signal to a nervous system of the wearer, the output signal being indicative of the estimate of the tilt of the wearer. Estimating tilt includes taking remedial action in response to the estimate of tilt of the wearer. Taking remedial action includes deploying an airbag worn by the wearer. Generating a motion signal includes generating an accelerometer signal and generating a gyro signal, and processing the signal includes processing the accelerometer signal and processing the gyro signal. Generating a motion signal includes generating a total signal based on the accelerometer signal and the gyro signal. Processing the accelerometer signal includes determining an accelerometer quaternion, and processing the gyro signal includes determining a gyro quaternion. Processing the accelerometer signal includes determining accelerometer Euler angles, and processing the gyro signal includes determining gyro Euler angles. Processing the accelerometer signal further includes determining a first redundant Euler angle, and processing the gyro signal further includes determining a second redundant Euler angle. Generating a total signal includes combining the accelerometer signal and the gyro signal by using a Kalman filter.

Other aspects include other combinations of the features recited above and other features, expressed as methods, apparatus, systems, program products, and in other ways. Other features and advantages will be apparent from the description and from the claims.

DETAILED DESCRIPTION

The Prosthesis

Figure 1:
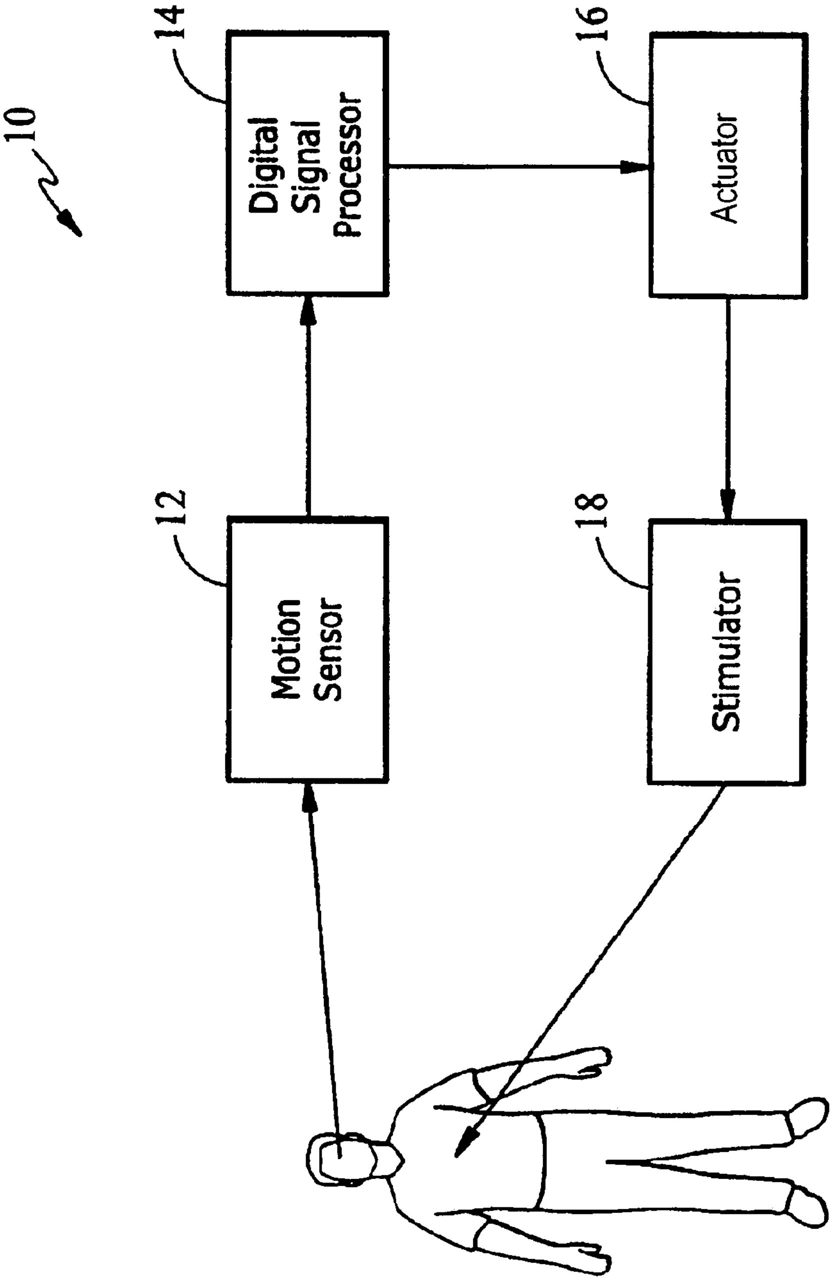
FIG. 1 is a block diagram of a balance prosthesis.

Referring to FIG. 1, a portable balance prosthesis 10 includes a motion sensing system 12. Motion sensing system 12 has an output that depends on the rotational and translational motion experienced by the wearer. The output from the motion sensing system 12 is provided to an on-board digital signal processor 14 that provides real-time estimates of the wearer's orientation and angular velocity in three-dimensional space. The processor 14 detects the wearer's vertical orientation while rejecting errors caused by instrument drift and extraneous acceleration. The resulting estimates are then provided to an actuator 16 that drives a stimulator 18 in communication with the wearer's nervous system. The actuator 16 translates the real-time estimates of the wearer's orientation and velocity into a form that can be used by the wearer. A controller area network (CAN) bus and controllers are provided to transfer information between the sensors, the digital processor, and the stimulator. The prosthesis also preferably includes a wireless transmitter, which allows system parameters such as dead zone and control loop gains to be adjusted and which allows subject performance to be remotely recorded. The prosthesis also may have one or more batteries that supply power to the sensors, processor, and stimulator.

The motion sensing system 12 is preferably an instrument sensor assembly (ISA). The ISA may include three gyroscopes ("gyros") and three accelerometers, but any number of any instruments capable of determining linear or angular changes in position may be used. Other such instruments include, for example, magnetometers.

Micromachining or microelectromechanical systems (MEMS) techniques can be used to provide small and portable sensors, e.g., as described in A. Kourepenis, J. Borenstein, et al., *"Performance of MEMS Inertial Sensors," AIAA GN&C Conference*, August, 1998. The ISA preferably includes read-out electronics and digitizers, and a mechanism and bubble level for aligning the sensors with the subject's natural or comfortable vertical. A suitable, relatively low-cost ISA may be assembled using the type of sensors currently used in automobiles for air bag deployment and traction control, for example Analog Devices ADXL accelerometers and gyroscopes, or Silicon Sensing Systems gyroscopes, or Motorola accelerometers. Such accelerometers may have a thermal sensitivity of about 3 milligravity (mg) per ° C. and noise of about 0.23 mg/√Hz. The gyroscopes may have a thermal sensitivity of about 650°/h/° C. and noise at 470°/h/√Hz. Assembled ISAs exhibiting higher performance may be purchased from Honeywell, for example the HG1920 instrument sensor assembly. The HG 1920 ISA incorporates accelerometers whose thermal sensitivity is 0.3 mg/° C. and gyroscopes whose thermal sensitivity and noise are 10°/h/° C. and 5°/h/Hz, performance one to two orders of magnitude better than commercial automotive grade sensors.

Figure 2:
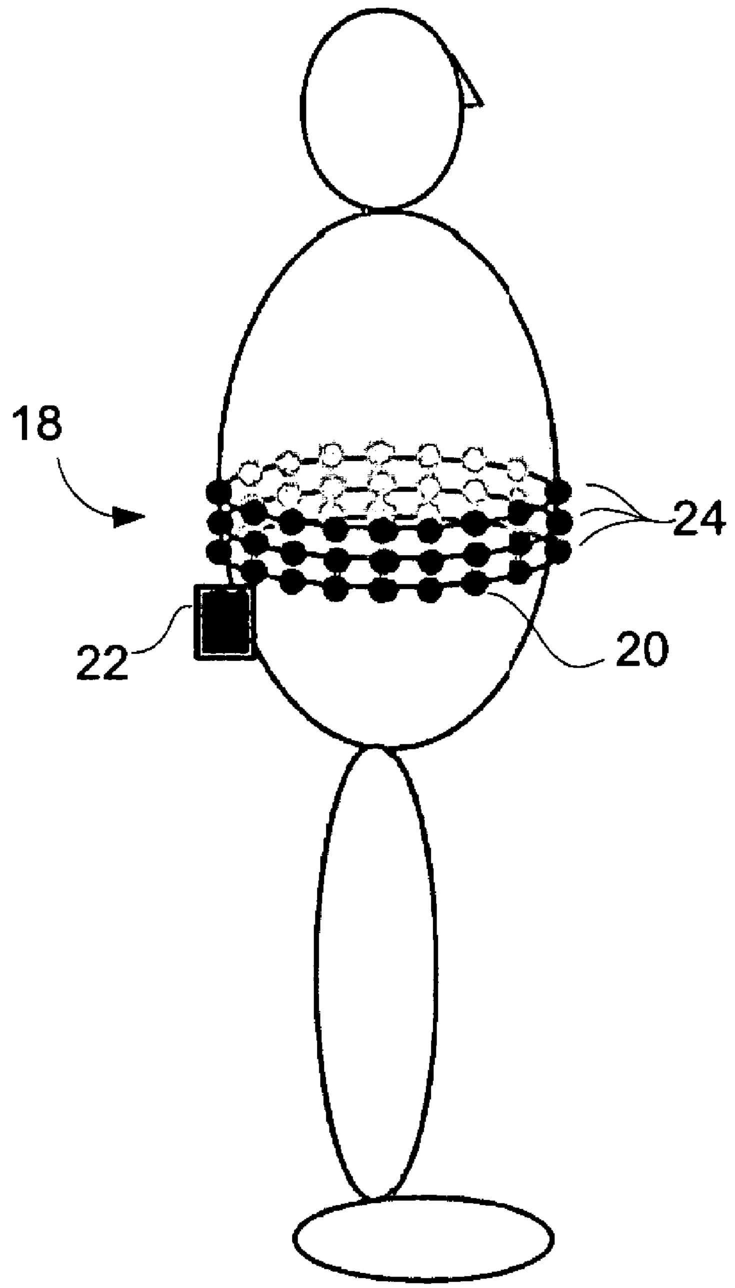
FIG. 2 is a diagram showing tactor locations on a subject.

Stimulator 18 preferably includes an array of tactors 20 (see FIG. 2) to be worn close to the subject's skin, e.g., in a belt around the subject's waist and/or in columns 24 (See FIG. 2) mounted on the subject's front and back. The tactors may be worn under or over clothing. Each tactor is an individually addressable electromechanical vibrating element. The array can include tactors to indicate azimuth and vertical tactor columns 24 to indicate elevation. "Azimuth" and "vertical," when describing tactors, are labels of convenience only; the phrases are not used to imply any structural difference between azimuth and vertical tactors. As determined by the preferences of the subject, there should be sufficiently many columns 24 to indicate the direction When energized, each tactor vibrates at a frequency that is readily perceived by the wearer, typically a frequency between 250 Hz and 400 Hz, e.g., 250 Hz. A digital controller commands individual tactor amplifiers, which drive the tactors.

The gyroscopic and accelerometer signals discussed above are processed to obtain a tilt-angle estimate. The tilt's direction is transmitted to the subject by the azimuth tactors and the tilt's magnitude is transmitted by the vertical tactors. The number of tactors is operator selectable, based e.g. on subject preference and sensitivity. The number of tactors can be selected based on other factors.

The prosthesis 10 also has at least one optional airbag 22. As described more fully below, the airbag is deployed when the subject is in a state in which a fall is imminent. In a preferred embodiment, the prosthesis is equipped with airbags that are positioned around the prosthesis so as to be effective if the subject should fall in any direction.

In addition to (or instead of) tactile stimulation, other forms of stimulation are possible, e.g. one or a combination of auditory or acoustic (L. Chiari, M. Dozza, et al., "Audio-biofeedback for balance improvement: an accelerometry-based system.," *IEEE Trans Biomed Eng*., Vol. 52, No. 12, 2005, p. 2108-11.) or electric currents applied to the tongue (P. Bach-y-Rita, K. A. Kaczmarek, et al., *"Form perception with a 49-point electrotactile stimulus array on the tongue: a technical note," J Rehabil Res Dev*, Vol. 35, No. 4, 1998, p. 427-30.) or skin.

Finding Vertical

The balance prosthesis converts sensor outputs to an indication of vertical and provides cues to the subject. For purposes of explanation, determination of the wearer's vertical will be presented in two parts: single axis tilt estimation, followed by the multi-axis estimations which may be used in the prosthesis.

Figure 3:
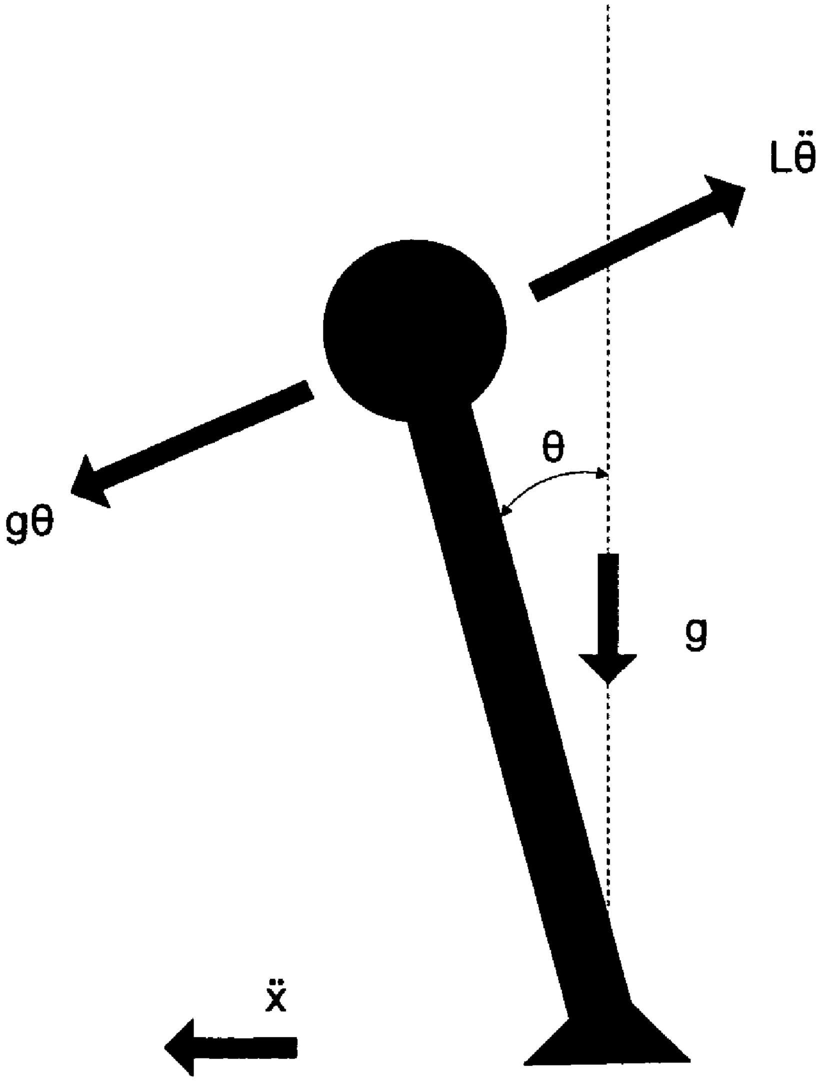
FIG. 3 is an inverted pendulum model of a standing person.

Referring to FIG. 3, the subject is modeled as an inverted pendulum with its fulcrum coinciding with the subject's feet. The subject is modeled as having a constant height L, and is assumed to be inclined at a tilt angle θ. In general, the tilt angle will be modeled as a function of time, since the subject is assumed to undergo motion. As used in this document, "motion" refers to all aspects of an object's movement, including but not limited to position, velocity, acceleration, trajectory, etc. Other, more refined, models can be employed, e.g. treating the subject as a double pendulum with fulcra at the subject's waist and at the subject's feet. The tilt estimations described below do not depend on a particular detailed model of the subject.

Single Axis Estimation

Figure 4:
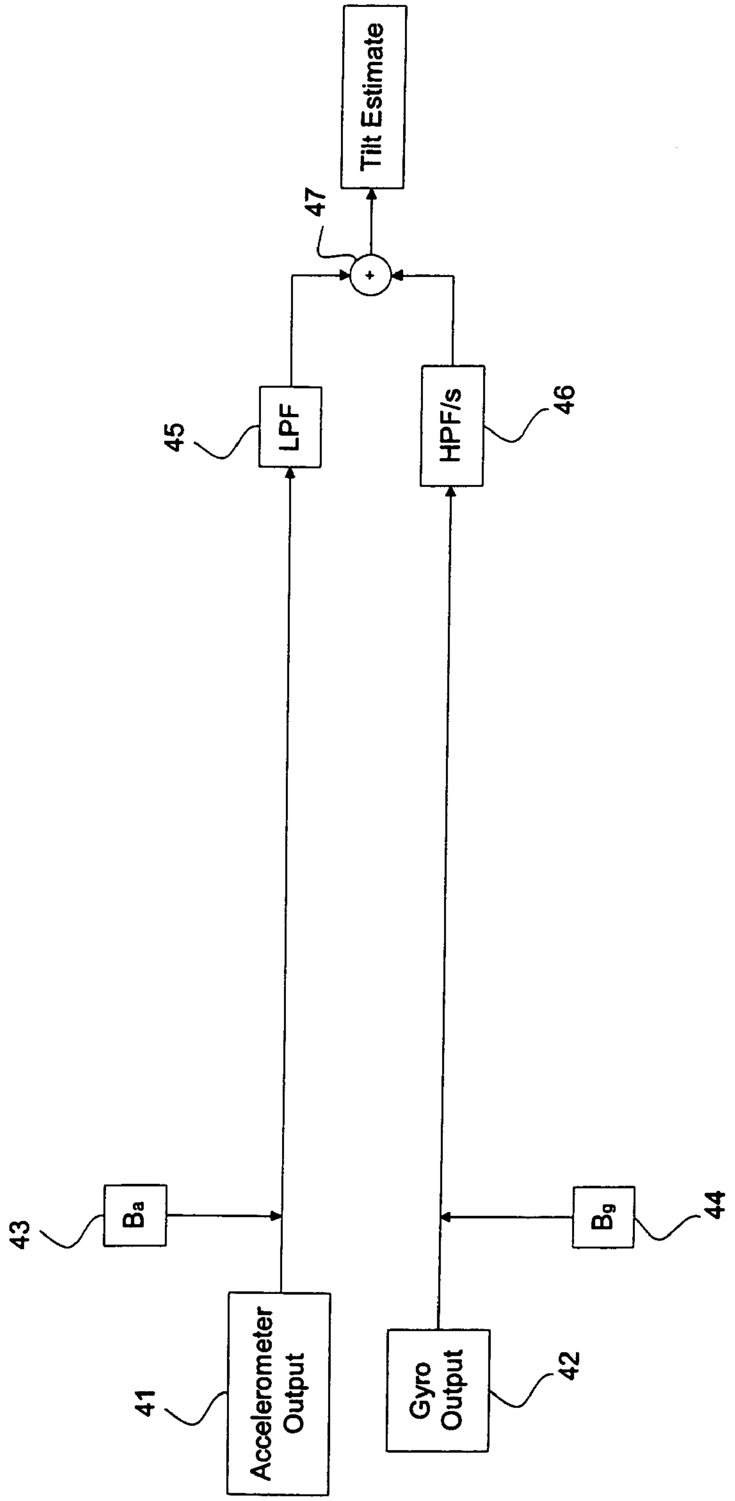
FIG. 4 is a block diagram illustrating single axis tilt estimation.

In "single axis estimation," motion experienced by the subject includes rotation about only one axis. A block diagram of a single axis estimation 40 used for the prosthesis is shown in FIG. 4. For instructional ease, analog filters are shown. Consistent with computer control, higher order digital filters also can also be used in the prosthesis.

As described more fully below, the single axis estimation determines the subject's tilt from gyro output 42 and accelerometer output 41. To mitigate the effects of gyro drift 44 and unwanted, high frequency acceleration inputs, the gyro output is filtered by a high-pass filter 46 and the accelerometer output is filtered by a low-pass filter 45. The outputs are then combined at a combiner 47, to produce the single-axis tilt estimation.

The voltage read from the accelerometer is modeled as:

$$V_a=S_a a+B_a \quad (1)$$

where, $S_a$ and $B_a$ are the scale factor and bias of the accelerometer and a is the acceleration which the accelerometer experiences. For ease of explanation, it is assumed that the subject's tilt angle and the initial offset angle of the accelerometer are small, allowing small-angle approximations to be employed. The estimation may be employed without making these approximations. Assuming small-angle approximations for the tilt angle θ and the initial offset α, the input acceleration is given by:

$$a=g(\theta+\alpha)-L\ddot{\theta}+a_h \quad (2)$$

Where g=acceleration due to gravity (9.8 m/s$^2$)

α=initial offset between accelerometer input axis and subject's vertical

L=Height of the subject, with the subject modeled as an inverted pendulum as shown in FIG. 3.

θ=angle between subject's position and subject's vertical $a_h$=horizontal acceleration of the pendulum pivot The gyro output is modeled as:

$$V_g=S_g\dot{\theta}+B_g \quad (3)$$

where, $S_g$ and $B_g$ are the scale factor and bias of the gyro respectively. To obtain a good estimate of tilt 0 and to remove the angular acceleration $\ddot{\theta}$ and horizontal acceleration $a_h$ from equation (2), the accelerometer output 41 should be low-pass filtered. For L=1.5 m, which is the height of a typical person, the angular acceleration term in (2) becomes larger than gθ for tilts with frequencies greater than 0.4 Hz. The angular acceleration term is 180 degrees out-of-phase with the desired tilt term so that wide bandwidth stabilization is difficult. To reduce the angular acceleration terms by two orders of magnitude, the break frequency of the low-pass filter is set at 0.03-0.3 Hz. The break frequency of the low-pass filter can be computed in this manner for a subject whose height is different from 1.5 m.

Since the gyro output is integrated in what follows, small bias can lead to large angle errors; however, the gyro gives a relatively good estimate of high-frequency rotation. To achieve a wide bandwidth estimate of the tilt angle θ, the gyro and accelerometer signals are combined. In analog Laplace transforms, the tilt is estimated by:

$$\hat{\theta}=LP(s)\left(\frac{V_a-\hat{B}_a}{\hat{S}_a}\right)+\frac{HP(s)}{s}\left(\frac{V_g-\hat{B}_g}{\hat{S}_g}\right) \quad (4)$$

where carat (^) denotes estimated or calibrated quantities stored in computation and LP(s) and HP(s) are the transfer functions of the low-pass filter 45 and high-pass filter 46:

$$LP(s)=\frac{s\omega_N^2(2\varsigma+1)+\omega_N^3}{(s+\omega_N)(s^2+2\varsigma\omega_N s+\omega_N^2)} \quad (5)$$

$$\frac{HP(s)}{s}=\frac{s^2+s\omega_N(2\varsigma+1)}{(s+\omega_N)(s^2+2\varsigma\omega_N s+\omega_N^2)} \quad (6)$$

where $\omega_N$=0.03 Hz, ζ=0.707, and s is the Laplace transform of the time derivative. In this document, references to a "low-pass filter" will mean a low-pass filter according to equation (5), and references to a "high-pass filter" will mean a high-pass filter according to equation (6), unless otherwise specified. Other low-pass or high-pass filters may be implemented with equal efficacy. The filters described above reduce accelerometer low frequency noise as the inverse of frequency squared. The low frequency gyro drift is proportional to frequency squared so that a bias shift does not result in a steady state offset of tilt. Filters of higher or lower order or direct digital implementations (such as impulse invariant) can be used as well.

The low-pass 45 and high-pass 46 filters are complementary; that is, HP(s)+LP(s)=1. Implementing the gyro filtering according to equation (6) avoids numerical problems associated with integrating the gyro rate and high-pass filtering later.

For error analysis and calibration, the estimated tilt is obtained from the actual tilt and other poorly modeled effects by substituting equations (1) through (3) into equation (4):

$$\hat{\theta} = LP(s)\left[\frac{S_a\left[g(\theta+\alpha) - L\ddot{\theta} + a_h\right] + B_a - \hat{B}_a}{\hat{S}_a}\right\} + \frac{HP(s)}{s}\left(\frac{S_g s\theta + B_g - \hat{B}_g}{\hat{S}_g}\right) \tag{7}$$

Errors in calibration or changes in bias are included in equation (7) by including both the actual bias and the bias obtained from calibration. Because of the third order high-pass filter 46 described by equation (6), gyro bias errors 44 do not cause a steady shift in the estimated tilt. White gyro noise does not cause angle random walk. The effects of accelerometer noise (the unmodeled bias terms) and angular and lateral accelerations decrease two decades per decade beyond the filter break frequency of 0.03 Hz.

Initialization

When starting the prosthesis, the subject is held still for 1 second at his comfortable vertical. In this position, the subject's tilt θ is defined to be 0. Because the subject is held still, by equation (1) the measured accelerometer voltage equals the accelerometer's estimated bias 43. By equation (2), the estimated bias 43 will contain the accelerometer-to-subject misalignment α.

$$\hat{B}_a = B_a + S_a g\alpha \tag{8}$$

Inserting equation (8) into equation (7), causes the calibration to account for the misalignment, a result that requires that the accelerometer input axis be close to, but not necessarily exactly, horizontal. (If the nominal accelerometer bias is known beforehand, unknown residual alignment is calibrated.) During calibration, a new gyro bias 44 is also determined in a similar manner by (3). Calibrating the accelerometer and gyro biases 43 and 44 greatly reduces any filter startup transients.

The balance prosthesis estimates the vertical to within 0.1 to 1 deg. A 1 mg (0.0098 m/s$^2$) accelerometer bias shift causes a 0.001 radian (0.06-deg) tilt error. Since the bias is calibrated at instrument turn-on, it must be maintained for roughly 16 hours. With 0.03 Hz filtering, accelerometer white noise of 1 mg/√Hz results in 0.2 milliradians of tilt. The best MEMS sensors can provide a stability of 1 mg, while 5 to 50 mg is typical of automotive grade sensors. Because the gyro signal is filtered to eliminate bias, accelerometer bias, not gyro bias, is the limiting factor in this processing scheme. The gyro contributes only transient errors. With the 0.03-Hz filters, 360-°/h/√Hz gyro white noise, typical of automotive sensors, results in 0.10 tilt error. The maximum allowable transient tilt error for a balance impaired subject to fall is not presently known.

Limitations of the Single-Axis Estimation

The ability to estimate the tilt that results from complicated motion including rotation about multiple axes is desirable, because such complicated motion more closely describes people in day-to-day tasks than does motion limited to rotation about a single axis. One simple strategy to estimate multi-axis tilt is that of employing several instrument sensor assemblies along multiple axes, each configured to perform single-axis tilt estimation.

This strategy provides reasonable tilt estimation for small tilt angles, but is otherwise flawed. Each instrument sensor assembly has a corresponding axis about which it detects the tilt of the subject. The single-axis tilt estimation is based in part on the instruments having particular spatial orientations relative to each other. When the subject rotates about the assembly's axis, the relative spatial orientations of the instruments are not changed in a manner which affects the estimation. However, when the subject rotates about an axis other than the axis corresponding to the assembly, the assembly's instruments' relative orientations change in a manner which will affect the estimation performed by the assembly. In essence, the single-axis assembly does not account for its own tilt about an axis different from the one it measures tilt relative to.

For sufficiently large angles, the change in the instruments' relative orientations leads to significant errors. For example, when the subject undergoes motion which includes a 45 degree rotation about two distinct axes, an estimate of the subject's tilt made by combining two single-axis tilt estimates may be off by as much as 20 degrees. For the general multi-axis and large angle case, one expands the single-axis estimation discussed to account for the changes in the spatial orientations of the instruments that occur as the subject rotates about multiple distinct axes.

As described in more detail below, the multi-axis algorithm can be implemented using quaternions. However, other implementations are possible, such as the use of Euler angles and Kalman filters. The following description of the multi-axis implementation relies on the following basic principles and notational conventions for quaternions.

Conventions for Quaternions

A quaternion is a particular type of number. As used herein, a quaternion has four parameters, also called components. The first parameter is sometimes referred to as "real," while the last three parameters are sometimes referred to as "complex." The symbols i, j, and k are often used to signify the three complex parameters. We may write a general quaternion by specifying its four parameters, for example:

$$\begin{aligned} Q &= [q_1, q_2, q_3, q_4] \\ &= q_1 + q_2 i + q_3 j + q_4 k \end{aligned} \tag{9}$$

It will often be convenient to use capital letters (e.g., Q) to represent a quaternion, and corresponding lower case letters with indices (e.g., $q_1$, $q_2$, $q_3$, $q_4$) to represent its components.

Quaternions can be multiplied. One way to define quaternion multiplication of quaternions Q and P with components [$q_1$, $q_2$, $q_3$, $q_4$] and [$p_1$, $p_2$, $p_3$, $p_4$] respectively, is to define the components of their product, denoted Q**P as:

$$Q ** P = \begin{bmatrix} p_1q_1 - p_2q_2 - p_3q_3 - p_4q_4 \\ p_2q_1 + p_1q_2 + p_4q_3 - p_3q_4 \\ p_3q_1 - p_4q_2 + p_1q_3 + p_2q_4 \\ p_4q_1 + p_3q_2 - p_2q_3 + p_1q_4 \end{bmatrix} \tag{10}$$

(where the top component is the first component.) Equivalently, quaternions represented using the "i, j, k" notation can be multiplied like ordinary polynomials subject to the rules $i^2=j^2=k^2=ijk=-1$. Note that quaternion multiplication is not commutative. That is, QP need not equal PQ.

The "conjugate" of a quaternion Q is defined by:

$$\text{conjugate}(Q)=[q_1,-q_2,-q_3,-q_4]. \quad (11)$$

Some quaternions can be used to describe geometric points in space, or vectors. When the real component of a quaternion equals 0, the three complex components can be thought of as representing the three Cartesian coordinates of a point in space. Equivalently, the three complex components can be used to define a vector in space anchored to the origin. For this reason, the first component of a quaternion is sometimes referred to as the "scalar" component, and the last three components are referred to as "vector" components.

Some quaternions can also define rotations of the vectors (and equivalently, reference frames). A quaternion Q can define a rotation if and only if its components satisfy the condition:

$$q_1^2+q_2^2+q_3^2+q_4^2=1 \quad (12)$$

In this case, the quaternion Q can be referred to as a "rotation quaternion." The square root of the expression on the left hand side of equation (12) is called the "magnitude" of the quaternion $Q=[q_1, q_2, q_3, q_4]$.

Suppose coordinate frame A is related to coordinate frame B by a rotation, with the rotation being described by a quaternion Q. Then the coordinates of a vector defined in coordinate frame A are related to the coordinates of the vector in coordinate frame B by:

$$\vec{V}_B=Q^{}\vec{V}_A{}^{}\text{conjugate}(Q) \quad (13)$$

(where the vectors in both coordinate frame A and coordinate frame B are assumed to be written in quaternion form, as described above.) The rotation quaternions are related to the angular velocity of the reference frame by:

$$\dot{Q} = \frac{Q ** \vec{\omega}^p}{2} \quad (14)$$

where $\vec{\omega}^p$ is the angular rotation rate of frame A with respect to frame B, expressed in the coordinates of frame A.

Equation (14) is particularly useful for inertial guidance or for an all gyro balance prosthesis, because the angular rates are measured directly (after bias and misalignment compensation) by the three gyroscopes. The integrations are straightforward for first order differential equations with no singular points.

Assume that coordinate frame A is obtained by rotating an angle θ about the z axis of coordinate frame B. The quaternion describing vector transformations from frame B to frame A is given by:

$$Q = \left[ \cos\left(\frac{\theta}{2}\right) \;\; 0 \;\; 0 \;\; -\sin\left(\frac{\theta}{2}\right) \right] \quad (15)$$

More generally, the amplitude of the rotation is defined by the scalar vector of the quaternion. The "axle" about which the rotation is executed is defined by the vector component of the quaternion. Note that the quaternion representing transformation from frame A back to frame B is given by the conjugate of the transformation from frame B to frame A. This is equivalent to replacing the angle by its negative.

Multi-Axis Tilt Estimation

Reference Frames

The multi-axis tilt estimation algorithm will perform calculations in a number of different reference frames, which are defined here. In general, "a reference frame" is a set of axes which can be used to specify the location of a point or an object in space. An "orthogonal" reference frame is one in which the axes are mutually perpendicular. The term "coordinate frame" is synonymous with "reference frame." To specify the location of a general point in space, at least three axes are required. For a given reference frame, these axes are typically labeled "x," "y," and "z." When multiple reference frames are under consideration, primes (') will be used to distinguish, e.g., the x-axis in one reference frame with the x'-axis of another.

The "local frame" is defined to be an orthogonal frame oriented with respect to the Earth so that its z-axis is aligned with the direction of gravity. In this definition, the Earth can be considered flat and the rotation of the Earth can be considered negligible. The x and y axes may be defined in any convenient way, so long as the local frame remains orthogonal. For example, the x and y axes of the local frame may be chosen to correspond to the nominal x and y axes of the body frame, as described below.

The "body frame" is attached to the subject's trunk or head, with the z-axis lying substantially parallel to the subject's spine. In the preferred embodiment, the z-axis is oriented so that movement in the positive z-direction corresponds to movement from the subject's head to the subject's feet. If the subject is standing with his arms outstretched in a "T" formation, the y-axis is oriented to be generally parallel to the subject's outstretched arms (with the positive y coordinates lying to the subject's right). The x axis is oriented to be generally perpendicular to the subject's chest (with positive x coordinates lying in front of the subject).

The roll, pitch, and yaw axes are synonymous with the x, y, and z axes of the body frame, respectively. Coordinates of a point as measured in some reference frame may be converted to coordinates measured in the body frame by conventional methods if the pitch, roll, and yaw angles are known.

Figure 5A:
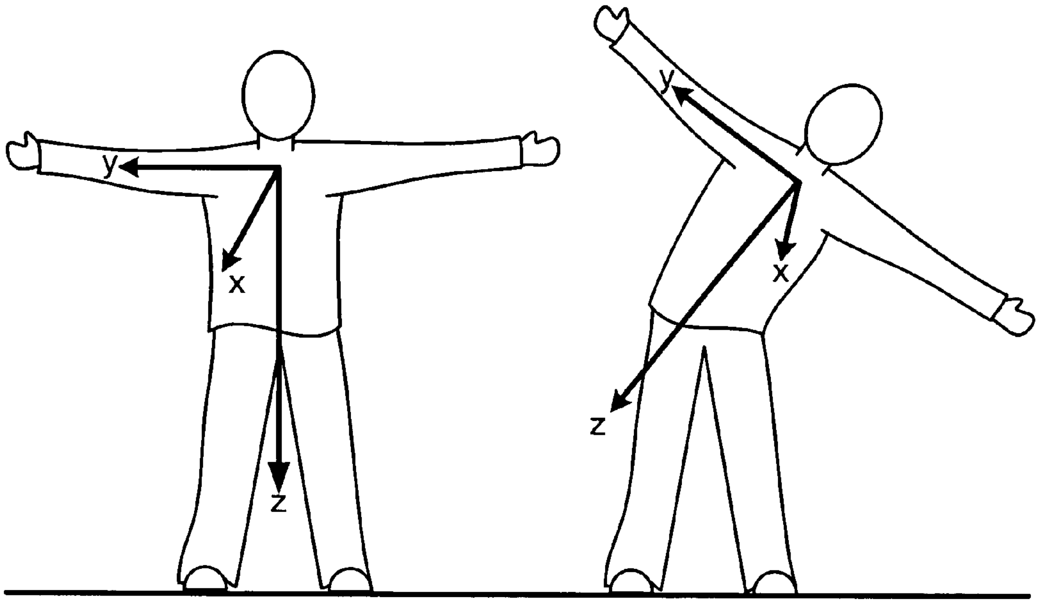
FIG. 5A is a reference frame centered on the subject's body.

In FIG. 5A, a subject is shown in two positions. When standing generally upright, the x, y, and z axes of the body frame are as indicated on the left. When bending over, the x, y, and z axes of the body frame are as indicated on the right.

The "platform frame" is an orthogonal frame defined by the input axes of inertial instruments. Alternatively, the platform frame can be defined by reference surfaces upon which the instrument sensor assembly is mounted. The prosthesis contains six instruments: three gyros and three accelerometers. Each instrument has its own input axis. The input axis of an instrument determines what the instrument measures: an accelerometer measures acceleration in the direction of its input axis, and a gyro measures rotation about its input axis.

Ideally, the accelerometers' input axes would all be mutually perpendicular, and the gyros' input axes would all be mutually perpendicular. (Equivalently, pairs of accelerometer input axes or pairs of gyro axes would coincide with reference surfaces). These cases are ideal because the input axes of the prosthesis can then be used to define an orthogonal frame in which the prosthesis has a fixed orientation. However, it is often impractical to install the accelerometers and the gyros with this precision, or to expect the sensors' axes to be aligned with a reference surface.

Figure 5B:
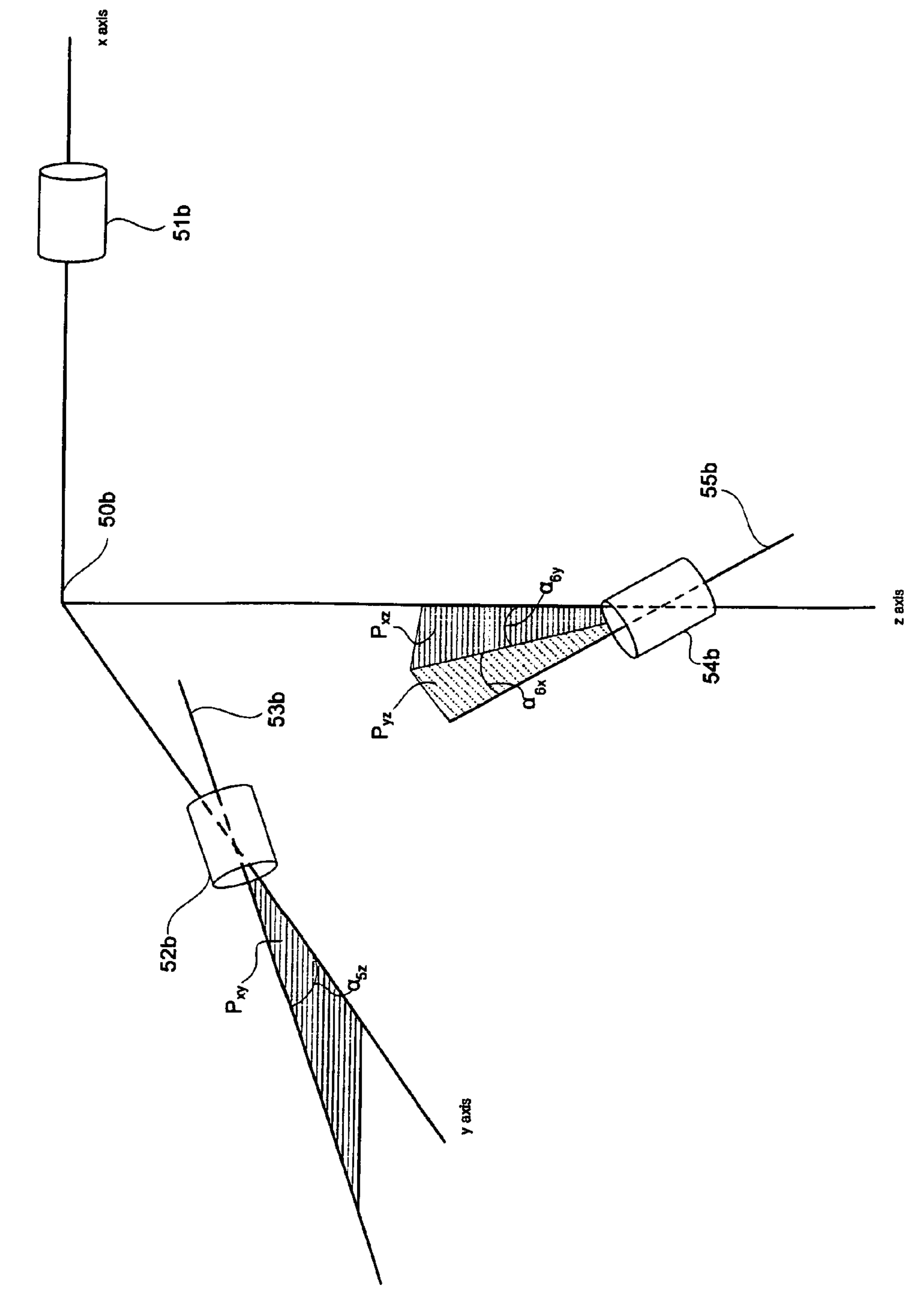
FIG. 5B is a reference frame centered on the platform.

Referring to FIG. 5B, the platform frame 50*b* may be defined as follows. Any of the six instruments in the prosthesis is selected arbitrarily. For illustration, an accelerometer 51*b* is selected, although the following procedure can be carried out using a gyro. The x axis of the platform frame is defined to coincide with the input axis (not shown) of the accelerometer 51*b*.

The input axes 53*b*, 55*b* of the remaining accelerometers 52*b*, 54*b* generally do not coincide with the platform axes, because the input axes 53*b*, 55*b* of the accelerometers need not be mutually perpendicular and the platform axes must be. Thus, there generally are two "misalignment angles" between each accelerometer's input axis and a given platform axis. To define the y axis of the platform frame, a second accelerometer 52*b* is selected, and the y axis is chosen so that this second accelerometer is misaligned with the y axis with only one nonzero angle of misalignment. In describing misalignment angles, subscripts 1-3 shall indicate gyros, subscripts 4-6 will indicate accelerometers, and the subscript x, y, or z will indicate the axis about to which the instrument should rotate to eliminate the misalignment. Thus, the misalignment angle is of the second accelerometer 52*b* is denoted $\alpha_{5z}$, because the accelerometer 52*b* is rotated by this angle about the z axis from aligning with the y axis.

The choice of they axis fixes the z axis, because the platform axes must be mutually perpendicular. Generally, there are two nonzero misalignment angles for the third accelerometer, denoted $\alpha_{6x}$ and $\alpha_{6y}$. (For clarity in FIG. 5B, planar regions $P_{xy}$, $P_{xz}$ and $P_{yz}$, parallel to the x-y, x-z and y-z planes, respectively are shown. Points of input axis 53*b* rotated about the z axis remain in the planar region $P_{xy}$, points of input axis 55*b* rotated about the y axis remain in the planar region $P_{xz}$, and points of input axis 55*b* rotated about the x axis remain in the planar region $P_{yz}$.) Generally, the input axes 53*b*, 55*b* of the accelerometers 52*b*, 54*b* are nearly parallel to the platform axes, so that one can refer to, e.g., a "nominally y accelerometer" as being the accelerometer whose input axis is closest to they axis of the platform frame. In this context, "nominally" implies that the input axis of the instrument in question need not exactly coincide with the specified axis. The nominally x, y, and z accelerometers 51*b*, 52*b*, 54*b* respectively are shown in FIG. 5B.

Figure 5C:
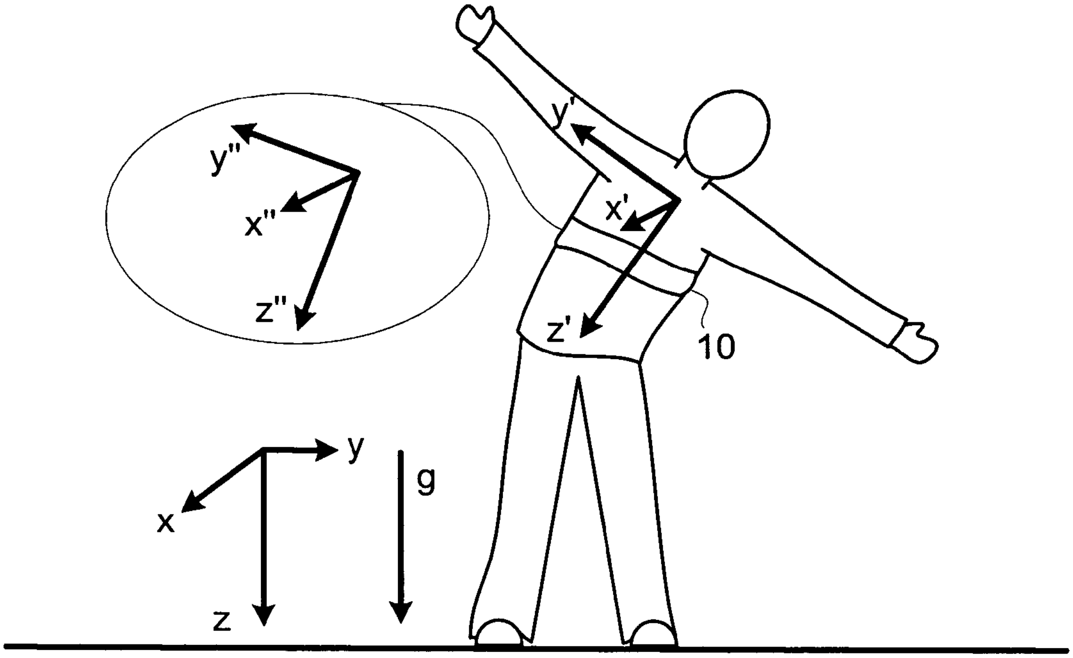
FIG. 5C is an illustration showing various reference frames in a single situation.

FIG. 5C shows a subject 50*c* (shown schematically) leaning forward while wearing the prosthesis 51*c* (shown schematically), with all of the reference frames described above shown. The direction of gravity is indicated by the arrow g. The local frame is labeled by x, y, and z axes. Note that the z axis is parallel to the direction of gravity. The body frame is labeled by x', y', and z' axes. Note that the z' axis is parallel to the subject's torso 52*c*. The platform frame is labeled by x", y", and z" axes. Note that no axis of the platform frame is parallel to any axis of the body frame. I.e., the body-to-platform misalignment angles are all nonzero.

The above reference frames are each convenient for particular tasks or contexts. For example, the local frame is a convenient frame in which to calculate the effect of gravity on the individual instruments, because gravity is always aligned with the local frame's z axis. The platform frame is a convenient frame to in which to manipulate the data obtained by all the instruments, because in the platform frame the instruments have a fixed position. The body frame is a convenient frame to make calculations related to presenting stimulus to the subject, so that the subject need not make mental calculations to make sense of the stimulus. Other tasks or calculations are convenient in each of the above reference frames.

Relation Between Platform and Sensor Frames

Assuming small misalignment angles, the transformation matrix relating coordinates in the body frame to those of the platform frame are given by:

$$C_b^p = \begin{bmatrix} 1 & \beta_z & -\beta_y \\ -\beta_z & 1 & \beta_x \\ \beta_y & -\beta_x & 1 \end{bmatrix} \quad (16)$$

where β=misalignment angle about subscripted axis of the platform frame. Calibrating the misalignment angles between the platform frame and the body frame is discussed in the "Initialization" sections after equations (7) and (31).

The misalignment of the other accelerometer input axes with respect to the platform axes are defined by the non-orthogonal matrix:

$$C_p^a = \begin{bmatrix} 1 & 0 & 0 \\ -\alpha_{5z} & 1 & 0 \\ \alpha_{6y} & -\alpha_{6x} & 1 \end{bmatrix} \quad (17)$$

where the α terms are the misalignment angles of the accelerometers with respect to the platform frame, defined above.

The misalignment of the gyroscope input axes with respect to the platform axes is defined by the non-orthogonal matrix:

$$C_p^g = \begin{bmatrix} 1 & \alpha_{1z} & -\alpha_{1y} \\ -\alpha_{2z} & 1 & \alpha_{2x} \\ \alpha_{3y} & -\alpha_{3x} & 1 \end{bmatrix} \quad (18)$$

where the α terms are defined analogously to the accelerometer case, as described above.

The general approach to determining the tilt angles of the subject is to detect the direction of gravity in the platform frame. Both accelerometer and gyro information is used to determine this. In one implementation, the direction of gravity as determined by each of the accelerometers and gyros can be displayed as a quaternion. In one implementation, quaternions determined from the accelerometers and from the gyros are combined to obtain a total quaternion. The total quaternion provides a more reliable estimate of the subject's tilt because the individual gyro or accelerometer quaternions have been filtered prior to being combined. As with the single-axis case, filtering removes errors associate with drift, bias, or noise of the respective instruments.

The Gyro Quaternion $Q_g$

Figure 6:
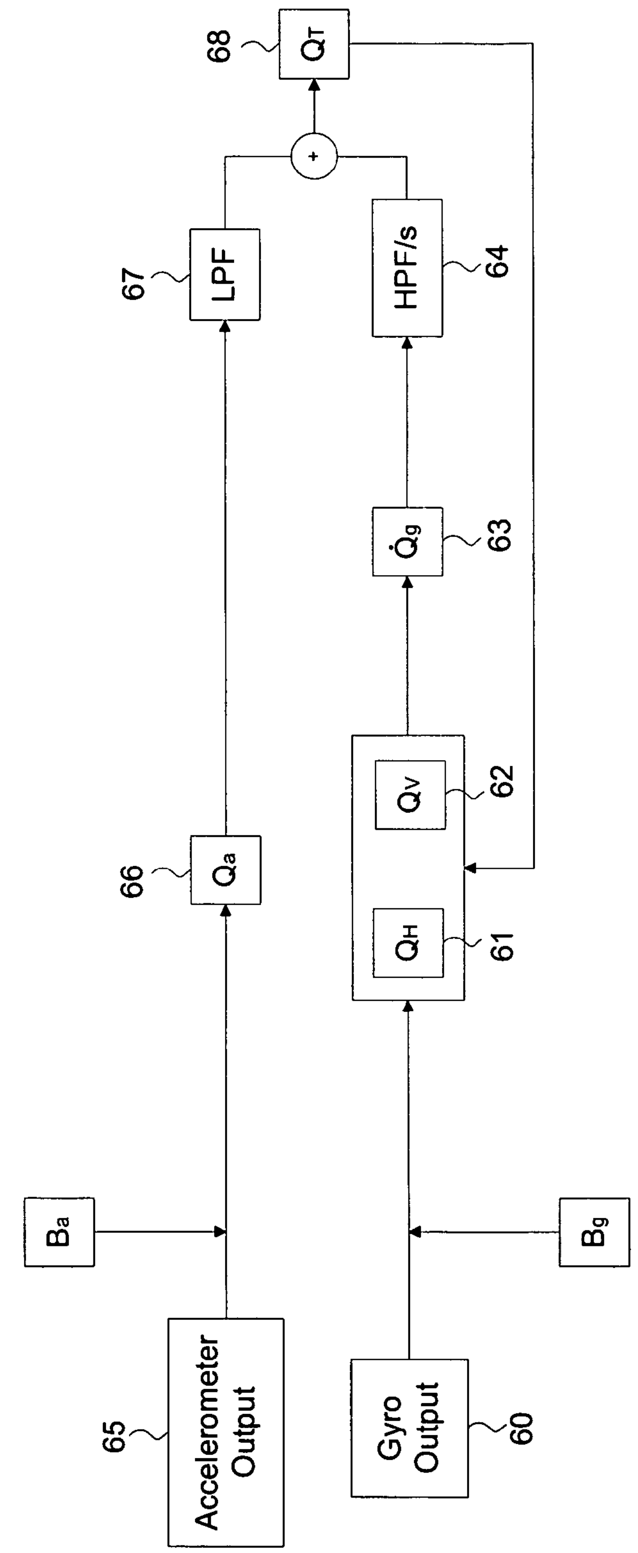
FIG. 6 is a block diagram illustrating a multi-axis tilt estimation using quaternions.

FIG. 6 shows a multi-axis estimate of the subject's tilt using quaternions. A gyro quaternion 63, denoted $Q_g$ will be used to rotate the platform frame into the local frame. From the gyro output 60 one can directly calculate the gyro quaternion 63. By separating the orientation into a rotation about the vertical and a rotation about the horizontal, as will be described below, a horizontal quaternion 61 is calculated without knowledge of azimuth and is independent of azimuth gyro drift (which can be difficult to directly determine). As in the single axis case, drift in the nominally horizontal gyro is removed by using the accelerometers for low frequencies.

The gyro quaternion $Q_g$ in FIG. 6 is defined as $$Q_g = Q_V ** Q_H \quad (19)$$

Where $$Q_V = \left[ \cos\left(\frac{\theta}{2}\right) \;\; 0 \;\; 0 \;\; \sin\left(\frac{\theta}{2}\right) \right],$$

a rotation quaternion about the vertical

θ=rotation about the vertical of inertial space with respect to the platform $Q_H = [h_1\ h_2\ h_3\ 0]$, a rotation quaternion about the horizontal

** indicates quaternion multiplication

Thus, $Q_g$ transforms a vector in the platform frame to the local frame by rotating an appropriate angle about a horizontal axis, followed by an appropriate rotation about a vertical axis. The quaternion $Q_H$ implementing the horizontal rotation is called the horizontal quaternion 61, and the quaternion $Q_V$ implementing the vertical rotation is called the vertical quaternion 62. The angular rate of the platform with respect to inertial space, represented as a quaternion in the platform coordinate frame, is:

$$\vec{\omega}^p=[0,\omega_1^p\omega_2^p\omega_3^p]. \tag{20}$$

The angular rate of the platform can be measured by the gyroscopes after compensating for bias, scale factor, and angular misalignments. Using these measurements, one can determine the gyro quaternion 63 through the equation:

$$\dot{Q}_g = \frac{Q_g ** \vec{\omega}^p}{2}. \tag{21}$$

Substituting equations (19) and (20) into equation (21), one can then solve for the individual quaternion terms of $Q_H$. Additionally, θ is directly determined by integration of the θ' equation below, so that the vertical quaternion can be determined by equation (19). The substitution of equations (19) and (20) into equation (21) yields:

$$\begin{aligned} h_1'(t) &= \frac{1}{2}(-\omega_1 h_2(t) - \omega_2 h_3(t)) \\ h_2'(t) &= \omega_3 h_3(t) + \frac{\omega_2 h_2(t) h_3(t)}{2h_1(t)} + \omega_1\left(\frac{h_1(t)}{2} - \frac{h_3(t)^2}{2h_1(t)}\right) \\ h_3'(t) &= -\omega_3 h_2(t) + \frac{\omega_1 h_2(t) h_3(t)}{2h_1(t)} + \omega_2\left(\frac{h_1(t)}{2} - \frac{h_2(t)^2}{2h_T(t)}\right) \\ \theta'(t) &= \omega_3 + \frac{\omega_2 h_2(t)}{h_1(t)} - \frac{\omega_1 h_3(t)}{h_1(t)}, \end{aligned} \tag{22}$$

where the prime (') indicates differentiation with respect to time t. To avoid clutter, in (22), the superscript p has been dropped.

Note that none of the time derivatives includes the azimuth angle θ. This allows the high-pass filter 64 and low-pass filter to act on the gyro signal 60 and accelerometer signal 65 respectively, so that $h_1$, $h_2$, and $h_3$ will approach the accelerometer-determined values. The h terms determine the horizontal quaternion 61 as above, which transforms a vector from the platform coordinates to a frame rotating about the vertical at the yaw rate.

The Accelerometer Quaternion

The gyro output 60 is obtained by transforming angular rates from gyro to platform coordinates. Each gyro is linearly modeled as a scale factor plus bias. Linear cross-axis terms are included in the misalignment angles defined by equation (18). The platform rates are solved directly from the three instrument voltages:

$$\begin{bmatrix} V_1 \\ V_2 \\ V_3 \end{bmatrix} = \begin{bmatrix} B_1 \\ B_2 \\ B_3 \end{bmatrix} + \begin{bmatrix} S_1 & 0 & 0 \\ 0 & S_2 & 0 \\ 0 & 0 & S_3 \end{bmatrix} C_p^g \begin{bmatrix} \omega_1 \\ \omega_2 \\ \omega_3 \end{bmatrix} \tag{23}$$

where

V=instrument output voltage,

B=instrument bias,

S=instrument scale factor,

ω=rates measured in platform coordinates, and subscripts 1-3 refer to the individual gyros Low-pass filtering the accelerometer outputs avoids inclusion of lateral accelerations and distance from rotation centers. The accelerometer output 65, which is thus determined by gravity as defined in the platform frame, is:

$$\begin{bmatrix} V_4 \\ V_5 \\ V_6 \end{bmatrix} = \begin{bmatrix} B_4 \\ B_5 \\ B_6 \end{bmatrix} + \begin{bmatrix} S_4 & 0 & 0 \\ 0 & S_5 & 0 \\ 0 & 0 & S_6 \end{bmatrix} C_p^a \begin{bmatrix} -g_1 \\ -g_2 \\ -g_3 \end{bmatrix} \tag{24}$$

In which gravity is a negative acceleration. From the accelerometer output 65, one solves for the three components of acceleration in the platform frame. From the platform gravity vector, the measured gravity quaternion is defined as:

$$\vec{g}^p=[0,\hat{g}_1,\hat{g}_2,\hat{g}_3] \tag{25}$$

The rotation quaternion about a horizontal axis for rotating gravity from platform coordinates to earth-fixed coordinates is:

$$Q_a = \left[\cos\left(\frac{\varphi}{2}\right), \frac{\sin\left(\frac{\varphi}{2}\right)g_2}{\sqrt{g_1^2+g_2^2}}, -\frac{\sin\left(\frac{\varphi}{2}\right)g_1}{\sqrt{g_1^2+g_2^2}}, 0\right], \tag{26}$$

where ϕ is the angle of rotation satisfying:

$$\tan(\varphi) = \frac{\sqrt{g_1^2+g_2^2}}{g_3}, \; 0 \le \varphi \le \pi.$$

This quaternion, $Q_a$, is called the accelerometer quaternion 66. The zero in the fourth position of the accelerometer quaternion 66 specifies that the rotation is about a horizontal axis.

Blending of the Quaternions

The horizontal quaternion 61 determined by equation (19) and the accelerometer quaternion 66 determined by equation (26) are similar in form. A total quaternion 68 can be obtained by applying a high-pass filter 64 to the gyro quaternion 63 to remove gyro drift, and by applying a low-pass filter to the accelerometer quaternion 66, and combining the results:

$$\hat{Q}_T(s)=L_p(s)\hat{Q}_a(s)+H_p(s)\hat{Q}_g(s) \tag{27}$$

The Gyro Quaternion Differential Equations

If poor estimates of the h terms are used in equation (22), the derivative h' will be calculated inaccurately. Therefore, after an initial estimate is made, the derivatives are subsequently obtained from the total quaternion 68. That is, the gyro quaternion 63 updates (19) as according to the equations:

$$\begin{aligned} h_{1g}'(t) &= \frac{1}{2}(-\omega_1 h_{2T}(t) - \omega_2 h_{3T}(t)) \\ h_{2g}'(t) &= \omega_3 h_{3T}(t) + \frac{\omega_2 h_{2T}(t) h_{3T}(t)}{2h_{1T}(t)} + \omega_1\left(\frac{h_{1T}(t)}{2} - \frac{h_{3T}(t)^2}{2h_{1T}(t)}\right) \\ h_{3g}'(t) &= -\omega_3 h_{2T}(t) + \frac{\omega_1 h_{2T}(t) h_{3T}(t)}{2h_{1T}(t)} + \omega_2\left(\frac{h_{1T}(t)}{2} - \frac{h_{2T}(t)^2}{2h_{1T}(t)}\right) \end{aligned} \tag{28}$$

where the subscript "g" indicates a gyro quaternion from equation (22), the subscript "T" indicates a total quaternion from equation (27), and the $\omega_i$ terms indicate the angular rates measured by the respective gyros and transformed into platform coordinates.

Because the accelerometer quaternion 66 is determined from acceleration ratios, its magnitude is always equal to 1 as expected for a rotation quaternion. The total quaternion 68 is normalized to 1 but the gyro quaternion 63 is not. The complementary filters 64, 67 correctly extract the gyro quaternion's oscillating portion so that the total quaternion 68 is close to 1. The gyro quaternion 63 is inserted into the complementary filters 64, 67, which are numerically integrated by a second order Runge-Kutta (B. Carnahan, H. A. Luther, and J. O. Wilkes, *Applied Numerical Methods*, John Wiley And Sons, New York, 1969).

Additionally, small damping terms could be added to equation (28) so that numerical or physical instabilities dampen over time. The total quaternion terms in equation (28) could be replaced with the low-passed terms derived from the accelerometers.

Firing Tactors

The total quaternion 68 is used to determine when to fire tactors and which tactors to fire. The gravity in local coordinates, [0, 0, 0, g], is rotated by the conjugate of the total quaternion 68 to obtain the gravity in the platform frame. Normalized to 1, the gravity in platform coordinates is calculated from the total quaternion 68 by:

$$\hat{g}_x = -2h_{1T}h_{3T}$$

$$\hat{g}_y = 2h_{1T}h_{2T}$$

$$\hat{g}_z = h_{1T}^2 - h_{2T}^2 - h_{3T}^2 \qquad (29)$$

The term $h_{1T}$ defines the magnitude of the rotation as described in the *Convention for Quaternions* section above, or, by inspection of (29), all three terms can be employed.

$$\hat{\phi} = a\tan 2(\sqrt{\hat{g}^2 + \hat{g}_y^2}, \hat{g}_z)\ 0 \leqq \phi \leqq \pi \qquad (30)$$

The firing angle θ is the azimuth angle indicating the direction toward which the subject should move to correct his posture. The firing angle is measured from the roll axis about the positive (nominally down) yaw axis (in body coordinates) and is determined by:

$$\hat{\phi} = a\tan 2[\hat{g}_y, \hat{g}_x] + \pi = a\tan 2[-\hat{g}_y, -\hat{g}_x] = a\tan 2[-h_{2T}, h_{3T}] \qquad (31)$$

If the roll axis is up while the pitch axis is horizontal, the subject is leaning backward. In this case, the acceleration sensed by the x-axis accelerometer is positive, which means the sensed $g_x$ is negative. Consistent with (31), the front tactor will be commanded to vibrate. As another example, assume the subject leans forward and right. In this case, the x and y accelerometers will indicate positive gravity (negative acceleration). Therefore the tactors behind and to the left of the subject will vibrate.

Initialization of the Prosthesis

The tactors drive the subject to the nulls defined by the sensors' output signals. Because of the complementary filters 64, 67, the low frequency (below 0.03 Hz) null is determined by the accelerometers. The prosthesis is therefore initialized to align the subject's comfortable vertical with that indicated by the accelerometers. In addition, the sensors' bias (the output signal when no acceleration or angular rate is applied) can drift between factory (test station) calibration and field tests with subjects. Changing instrument bias is equivalent to the instrument's null changing with time.

Beforehand, on a test station, the prosthesis undergoes a stationary calibration in which each sensor's bias, scale factor, and the misalignment angles with respect to the ISA reference plane are calibrated. Because the balance prosthesis seeks to null the sensor outputs, the sensor bias, and particularly accelerometer bias, is generally more important than the scale factor. Thus, initialization focuses on instrument-to-platform and platform-to-body misalignment angles and sensor bias. The stationary calibration can be performed by measuring a lumped bias or by assuming the factory bias and determining the body-to-platform misalignments.

The lumped bias approach combines the accelerometer bias and alignment angles. The instrument sensory assembly (ISA) is mounted on the subject and adjusted to be nearly level, using, for example, a bubble level on the ISA. The leveling implies that the sensor input axes are close to horizontal and vertical. Thus, misalignments between the subject's vertical and the ISA are small angles. With assistance, the subject stands vertical long enough to accomplish the initialization, for example one second. With the assumption of no motion, the gyro outputs are recorded as gyro bias. Again assuming no motion, the horizontal accelerometer outputs contain sensor bias plus misalignment times gravity terms. These are automatically entered as a bias (the "lumped" bias). The lumped bias effectively nulls the accelerometers to the subject's comfortable vertical and removes accelerometer drift. At this point, the angles between the accelerometers and subject vertical are not known; however, for low frequency and steady state, the ISA will drive the subject to his vertical. Because the angles are not known, the knowledge of the vertical at high frequencies (gyro alignment is assumed small) and high roll and pitch angles is not perfect but sufficient for null-seeking prostheses. The periodic bias calibration allows less costly instruments to be used.

A second option is to assume that accelerometer bias is constant and does not require periodic recalibration. A third option is to provide a simple calibration fixture so that the sensors' bias can be measured immediately before mounting the ISA to the subject. Accelerometer bias can be calculated from the average of its outputs after the input axis is initially aligned up and then its alignment is reversed. This procedure is relatively insensitive to alignment angles and can be done without a precise test table. During the on-subject initialization, one can solve for the misalignments of the accelerometers and employ the factory-supplied misalignments of the gyros with respect to the accelerometers. One need not determine misalignment about the vertical, i.e., the azimuth alignment between the tactors and the ISA. Because the tactors are used in closed loop control, precise knowledge of azimuth alignment is not necessary.

Other Multi-Axis Embodiments

A number of embodiments of the invention have been described. Nevertheless, it will be understood that various modifications may be made without departing from the spirit and scope of the invention.

For example, vibrating elements other than tactors may be used to deliver information to the subject. Moreover, signals other than tactile signals can be provided to the subject. For example, an acoustic signal can be delivered through a headset or a visual signal can be delivered by selectively illuminating light sources.

Moreover, other multi-axis estimation methods may be used, for example estimates based on Euler angles, redundant Euler angles, or estimates made using a Kalman filter. Examples of these types of multi-axis estimates are given below.

Euler Angles

One way to uniquely specify the orientation of a body can be done using Euler angles. "Euler angles" are similar to misalignment angles described above. In this document roll, pitch, and yaw angles are used to describe Euler angles. Other angles may be used. The prosthesis determines the roll and pitch angles of the subject with respect to local coordinates as described below. Determining the yaw angle is of little importance, because motion consisting of purely changing yaw (e.g. standing still at the center of a slowly spinning merry-go-round) poses little danger to vestibulopathic subjects.

Coordinate Frames and Transformations

The transformation from local coordinates to the body frame is calculated by:

$$C_L^b = C_r C_p C_y, \tag{32}$$

where $$C_y = \begin{bmatrix} \cos(Y) & \sin(Y) & 0 \\ -\sin(Y) & \cos(Y) & 0 \\ 0 & 0 & 1 \end{bmatrix} \tag{33}$$

$$C_p = \begin{bmatrix} \cos(P) & 0 & -\sin(P) \\ 0 & 1 & 0 \\ \sin(P) & 0 & \cos(P) \end{bmatrix} \tag{34}$$

$$C_r = \begin{bmatrix} 1 & 0 & 0 \\ 0 & \cos(R) & \sin(R) \\ 0 & -\sin(R) & \cos(R) \end{bmatrix} \tag{35}$$

and P is the pitch angle, R is the roll angle, and Y is the yaw angle.

These transformation matrices are orthogonal. The pitch angle P is limited to $-\pi/2<P<\pi/2$. This is a mathematical, not physical, limitation related to the phenomenon of "gimbal lock." If operation near $P=\pm\pi/2$ is required, variables can be redefined (for example, exchange definitions of pitch and roll) or augmented (e.g., by adding a fourth Euler angle, as described below in *Redundant Gimbal Euler Angles*) to avoid the singularity. The angular rates sensed in the body frame are related to the derivatives of the Euler angles through:

$$\vec{\Omega}_{Lb}^{b} = C_{ypr}^{b} \begin{bmatrix} \dot{R} \\ \dot{P} \\ \dot{Y} \end{bmatrix} \tag{36}$$

$$C_{ypr}^{b} = \begin{bmatrix} 1 & 0 & -\sin(P) \\ 0 & \cos(R) & \cos(P)\sin(R) \\ 0 & -\sin(R) & \cos(P)\cos(R) \end{bmatrix} \tag{37}$$

For vectors, the subscript Lb indicates that the rate is that of the base with respect to the local frame and the superscript b indicates that the quantities are measured or defined in the body frame. Transformations (32) through (35) are orthogonal so that their respective transposes are also their inverses. Transformation (37), however, is not orthogonal.

The outputs of the gyros are obtained by transforming roll, pitch and yaw rates into components along the gyros' input axes. Each gyro is modeled as a simple bias plus scale factor. The output signals are:

$$\begin{bmatrix} V_1 \\ V_2 \\ V_3 \end{bmatrix} = \begin{bmatrix} B_1 \\ B_2 \\ B_3 \end{bmatrix} + \begin{bmatrix} S_1 & 0 & 0 \\ 0 & S_2 & 0 \\ 0 & 0 & S_3 \end{bmatrix} C_p^g C_b^p C_{ypr}^b \begin{bmatrix} \dot{R} \\ \dot{P} \\ \dot{Y} \end{bmatrix} \tag{41}$$

where the V terms represent the output voltages of each gyro, and $C_b^P$, $C_p^g$ are matrices given by equations (16) and (28) respectively. The gyro outputs are obtained from inserting equation (37) into equation (41):

$$\begin{bmatrix} V_1 \\ V_2 \\ V_3 \end{bmatrix} = \begin{bmatrix} B_1 \\ B_2 \\ B_3 \end{bmatrix} + C_p^g C_b^p \begin{bmatrix} S_1[\dot{R} - \sin(P)\dot{Y}] \\ S_2[\cos(P)\sin(R)\dot{Y} + \cos(R)\dot{P}] \\ S_3[\cos(P)\cos(R)\dot{Y} - \sin(R)\dot{P}] \end{bmatrix} \tag{42}$$

For small angles and small yaw rates, each gyro senses a single rate. This results in two single-axis feedback loops. As expected, the outputs in equation (42) do not depend on the yaw angle.

Considering only gravity inputs, the accelerometer outputs are determined by:

$$\begin{bmatrix} V_4 \\ V_5 \\ V_6 \end{bmatrix} = \begin{bmatrix} B_4 \\ B_5 \\ B_6 \end{bmatrix} + \begin{bmatrix} S_4 & 0 & 0 \\ 0 & S_5 & 0 \\ 0 & 0 & S_6 \end{bmatrix} C_p^a C_b^p C_L^b \begin{bmatrix} 0 \\ 0 \\ -g \end{bmatrix} \tag{43}$$

where the V terms represent the output voltages of the accelerometers. Equation (43) assumes that the accelerometer input axis is aligned nominally with +z (down) so that gravity causes a negative voltage. Including the body-to-platform and accelerometer-to-platform misalignments in the previous equation, the accelerometer outputs from gravity are:

$$\begin{bmatrix} V_4 \\ V_5 \\ V_6 \end{bmatrix} = \begin{bmatrix} B_4 + gS_4[\sin(P)] \\ B_5 - gS_5[\cos(P)\sin(R)] \\ B_6 - gS_6[\cos(P)\cos(R)] \end{bmatrix} + \begin{bmatrix} gS_4[-\beta_z\cos(P)\sin(R) + \beta_y\cos(P)\cos(R)] - \\ gS_5[\beta_x\cos(R)\cos(P) + (\beta_z + \alpha_{5z})\sin(P)] + \\ gS_6[(\beta_x + \alpha_{6x})\cos(P)\sin(R) + (\beta_y + \alpha_{6y})\sin(P)] \end{bmatrix} \tag{44}$$

This equation accounts for all the misalignment terms. A more detailed representation can also include lateral accelerations of the body frame. In what follows, the accelerometer outputs are low-pass filtered, to remove the effect of the lateral accelerations on the measurement. Thus, there is no need to account for them in equation (44).

Euler Angle Estimate

Figure 7:
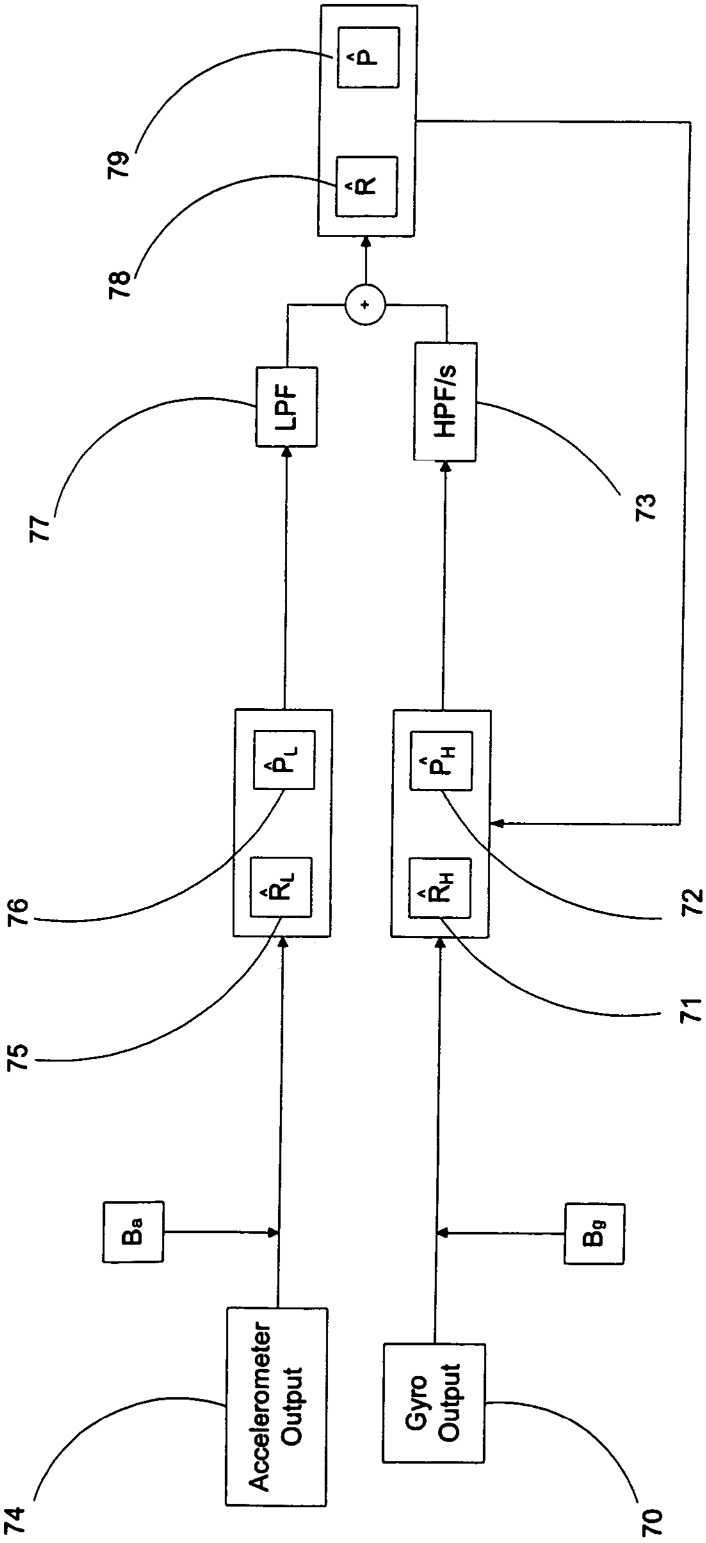
FIG. 7 is a block diagram illustrating a multi-axis tilt estimation using Euler angles.

FIG. 7 shows how the Euler angles of the subject are calculated. Either the gyro (42) or accelerometer (44) equations can be solved to obtain roll and pitch angles. The gyro equations determine a high-frequency roll estimate 71 and a high-frequency pitch estimate 72; and the accelerometer equations will determine a low-frequency roll estimate 75 and a low-frequency pitch estimate 76. Because the accelerometer signals contain angular and lateral accelerations and because gyro drift is integrated to obtain the roll and pitch, it is desirable to calculate the roll and pitch by low-pass filtering the output of the accelerometers and by high-pass filtering the output of from the gyroscopes.

The low-frequency roll estimate 75 and pitch estimate 76 are obtained from the accelerometer outputs 74 by inverting equation (44) and filtering through a low-pass filter 77:

$$\hat{R}_L = \text{atan2}\lfloor -\hat{a}_5^p, -\hat{a}_6^p \rfloor * L_p \tag{45}$$

$$\hat{P}_L = \text{atan2}\left[\hat{a}_4^p, -\frac{\hat{a}_6^p}{\cos\hat{R},}\right] * L_p \tag{46}$$

where $\hat{R}_L$, $\hat{P}_L$=low frequency portion of roll, and pitch estimates

*=convolution operator $L_p$=low-pass filter (see equation 5)

a tan 2=two argument arc tangent. Here a tan 2(yx)=a tan(y/x) in the first quadrant $\hat{a}^p$=acceleration in platform frame based on measurement in accelerometer frame, i.e.

$$\hat{a}^p = \hat{C}_a^p \begin{bmatrix} \hat{S}_4 & 0 & 0 \\ 0 & \hat{S}_5 & 0 \\ 0 & 0 & \hat{S}_6 \end{bmatrix}^{-1} \begin{bmatrix} V_4 - \hat{B}_4 \\ V_5 - \hat{B}_5 \\ V_6 - \hat{B}_6 \end{bmatrix},$$

$C_a^p=(C_p^a)^{-1}$=transformation matrix from accelerometers to platform frame. If needed the body to platform misalignments $C_b^p$ can be included.

For small pitch angles, the second variable in a tan 2 is roughly 1 g so that the small axis approximation holds. In equation (46), the roll estimated from both the gyros and accelerometers is used. Optionally, $\hat{R}$ in equation (46) can be replaced with $\hat{R}_L$. From equation (42), one obtains the Euler angle rates from the measured gyro outputs 70. These are, with misalignment angles omitted and high-pass filter 73 included, $$\dot{\hat{R}}_H = \left[\frac{\sin\hat{P}\cos\hat{R}(V_3 - \hat{B}_3)}{\hat{S}_3\cos\hat{P}} + \frac{\sin\hat{P}\sin\hat{R}(V_2 - \hat{B}_2)}{\hat{S}_2\cos\hat{P}} + \frac{(V_1 - \hat{B}_1)}{\hat{S}_1}\right] * H_p \tag{47}$$

$$\dot{\hat{P}}_H = \left[\frac{\cos\hat{R}(V_2 - \hat{B}_2)}{\hat{S}_2} - \frac{\sin\hat{R}(V_3 - \hat{B}_3)}{\hat{S}_3}\right] * H_p \tag{48}$$

$$\dot{\hat{Y}}_H = \left[\frac{\cos\hat{R}(V_3 - \hat{B}_3)}{\hat{S}_3\cos\hat{P}} + \frac{\sin\hat{R}(V_2 - \hat{B}_2)}{\hat{S}_2\cos\hat{P}}\right] * H_p \tag{49}$$

In equations (47)-(49), $H_p$ is the high-pass filter described by equation (6). The angular rates specified in equations (47)-(49) employ the combined roll 78 and pitch 79, as described in equations (50)-(51). This reduces accumulation of drift during gyro integration. The angular rates for roll and pitch can be directly integrated to obtain a high-frequency roll estimate 72 and a high-frequency pitch estimate 73.

The combined roll angle 78 and pitch angle 79 are defined as follows:

$$\hat{P}=\hat{P}_L+\hat{P}_H \tag{50}$$

$$\hat{R}=\hat{R}_L+\hat{R}_H \tag{51}$$

The high and low-pass filters are complementary. In Laplace transform notation:

$$H_p(s)=1-L_p(s) \tag{52}$$

The integral of yaw rate in equation (49) is not used since the yaw angle appears in no other expressions. The low-frequency roll estimate 75 and pitch estimate 76 do not depend on prior knowledge of the roll and pitch. As long as the accelerometer coefficients are known, the low frequency angles are determined and the subject will stand about his vertical on the average. Additionally, small damping terms could be added to equations (47) and (48) so that numerical or physical instabilities dampen over time. The total pitch and roll terms could be replaced with the low passed terms derived from the accelerometers.

Redundant Gimbal Euler Angles

Another approach involves a fourth, redundant Euler angle whose function is similar to the redundant gimbal in inertial navigation systems.

The redundant Euler angle is added to the traditional yaw, pitch, and roll angles. The redundant Euler angle is selected so that the pitch angle remains near null, thereby avoiding effective gimbal lock. This approach allows the accelerometers to estimate low frequency components of tilt (below 0.03-0.3 Hz) while the gyros estimate the higher frequency components without requiring low frequency yaw information. This formulation is useful because the accelerometers only yield information about tilt and not azimuth.

The redundant Euler angle is implemented as follows. The transformation from local coordinates to body coordinates is calculated by:

$$C_L^b=C_JC_rC_pC_y \tag{53}$$

where $C_r$, $C_p$, and $C_y$ are as above and $C_J$ is rotation about the redundant angle, defined by:

$$C_J = \begin{pmatrix} \cos(J) & 0 & -\sin(J) \\ 0 & 1 & 0 \\ \sin(J) & 0 & \cos(J) \end{pmatrix}. \tag{54}$$

The angular rates sensed in the body frame are related to the derivatives of the Euler angles through:

$$\vec{\Omega}_{Lb}^b = C_a^b \begin{bmatrix} \dot{J} \\ \dot{R} \\ \dot{P} \\ \dot{Y} \end{bmatrix}, \tag{55}$$

where $$C_a^b = \begin{pmatrix} 0 & \cos(J) & \sin(J)\sin(R) & -\cos(P)\cos(R)\sin(J) - \cos(J)\sin(P) \\ 1 & 0 & \cos(R) & \cos(P)\sin(R) \\ 0 & \sin(J) & -\cos(J)\sin(R) & \cos(J)\cos(P)\cos(R) - \sin(J)\sin(P) \end{pmatrix}$$

The subscript "Lb" indicates that the rate is that of the body with respect to the local frame and the superscript "b" indicates that the quantities are measured or defined in the body frame. The $C_a^b$ transformation is not orthogonal. For ease of explanation, it is assumed that the instruments are aligned with the body frame. This assumption can be relaxed by introducing additional transformations to account for misalignment, as was done above.

The gravity vector $g^y$ is fixed in the yaw frame and takes the form:

$$g^y = \begin{bmatrix} 0 \\ 0 \\ g \end{bmatrix}. \tag{56}$$

A vector defined in the yaw frame is transformed into body coordinates by the transformation:

$$C_y^b = \begin{pmatrix} \cos(J)\cos(P) - \cos(R)\sin(J)\sin(P) & \sin(J)\sin(R) & -\cos(P)\cos(R)\sin(J) - \cos(J)\sin(P) \\ \sin(P)\sin(R) & \cos(R) & \cos(P)\sin(R) \\ \cos(P)\sin(J) + \cos(J)\cos(R)\sin(P) & -\cos(J)\sin(R) & \cos(J)\cos(P)\cos(R) - \sin(J)\sin(P) \end{pmatrix} \tag{57}$$

For nominal position, the input axis of the yaw accelerometer is down and the yaw accelerometer will therefore detect gravity as a negative acceleration. The gravity vector in the body frame is:

$$g^b = \begin{bmatrix} -\cos(P)\cos(R)\sin(J) - \cos(J)\sin(P) \\ \cos(P)\sin(R) \\ \cos(J)\cos(P)\cos(R) - \sin(J)\sin(P) \end{bmatrix} g. \quad (58)$$

The roll, pitch, and yaw rates can be determined as functions of angular rates $\omega_x$, $\omega_y$, and $\omega_z$ sensed by the gyroscopes in the body frame by solving:

$$\dot{R}=\sin(J)(\omega_z-\omega_x\cos(R)\tan(P))+\cos(J)(\omega_x+\omega_z\cos(R)\tan(P))$$

$$\dot{P}=(-\omega_z\cos(J)+\omega_x\sin(J))\sin(R)+\cos(R)(\omega_y-\dot{J})$$

$$\dot{Y}=\sec(P)(\omega_z\cos(J)\cos(R))-\omega_x\cos(R)\sin(J)+\sin(R)(\omega_y-\dot{J}) \quad (59)$$

where P, R, J and Y, are functions of time. In addition to these three equations, a control law for both the accelerometer and gyro equations, $$\dot{J}=Pk_p \text{ if } \cos(R)\geqq 0, \text{ otherwise } \dot{J}=-Pk_p$$

is added, where $k_p$ is a positive constant. In an exemplary embodiment, $k_p$ is between 20 and 100 radians/second. Thus, a system of four equations in four variables is obtained. Such a system can be solved using ordinary methods. The solution, which is based on the outputs of the gyroscopes, can be combined with the accelerometer output as described above to yield a total measurement of the wearer's tilt.

Kalman Filter

Figure 8:
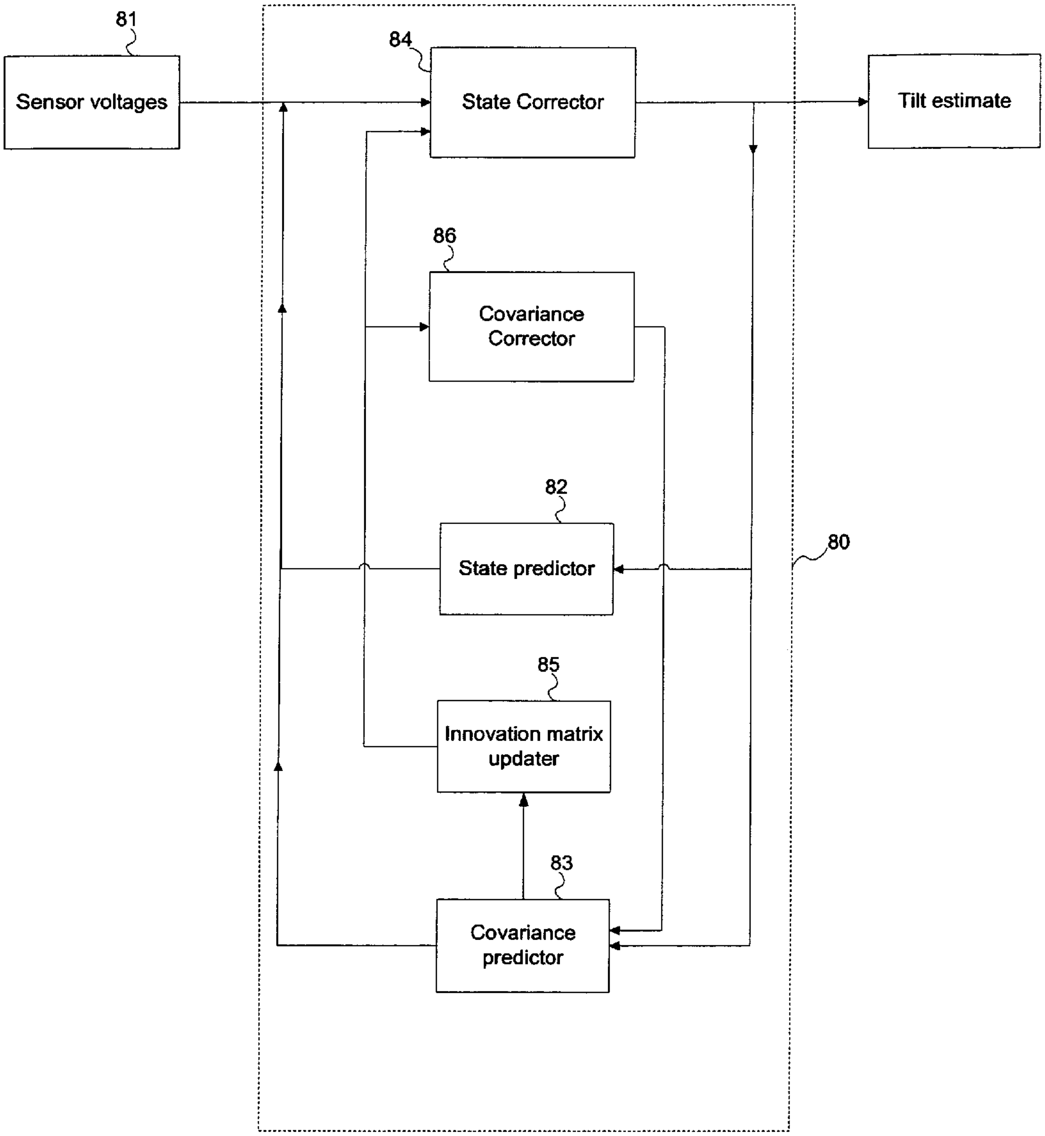
FIG. 8 is a block diagram illustrating a multi-axis tilt estimation using a Kalman filter.

FIG. 8 shows a thirteen-state extended Kalman filter 80 that can be used to obtain tilt estimates using the sensor platform. The thirteen states include six first-order Markov processes for low frequency sensor drifts, three first-order Markov processes for angular rate, and four states for propagating the quaternions representing the subject's tilt. It is emphasized that Kalman filters can be designed with more or fewer states, but that the underlying principles are similar. The Markov processes for the sensors coupled with the wide bandwidth noise on the sensor output shape the Kalman filter to a response similar to that of the high- and low-pass filters described above.

In this context, the gyro and accelerometer biases are modeled as first-order Markov processes and wide bandwidth noise. The body frame input angular rates are also modeled as first-order Markov processes. The angular rates are related to the quaternions, which define angular orientation, through the nonlinear first-order quaternion differential equation (14). Three gyro biases, three accelerometer biases, three angular rates, and four quaternions result in thirteen states.

For the sensor models, the Markov process appears in the state vectors while the wide bandwidth noise is output noise. In state space, the Markov processes for sensor bias and input angular rate are modeled as:

$$\frac{d\vec{x}_{1-9}}{dt} = A_{11}\vec{x}_{1-9} + B_1\vec{w} \quad (60)$$

$$\vec{x}_{1-9} = [\, B_{g1} \;\; B_{g2} \;\; B_{g3} \;\; B_{a1} \;\; B_{a2} \;\; B_{a3} \;\; \omega_1 \;\; \omega_2 \;\; \omega_3 \,]^T \quad (61)$$

$$B_1 = diag[\, \omega_g \;\; \omega_g \;\; \omega_g \;\; \omega_a \;\; \omega_a \;\; \omega_a \;\; \omega_\theta \;\; \omega_\theta \;\; \omega_\theta \,] \quad (62)$$

$$A_{11} = -B_1 \quad (63)$$

$$w = [\, B_{gn1} \;\; B_{gn2} \;\; B_{gn3} \;\; B_{an1} \;\; B_{an2} \;\; B_{an3} \;\; \omega_{n1} \;\; \omega_{n2} \;\; \omega_{n3} \,]^T, \quad (64)$$

where $\vec{x}_{1-9}$ represents a state vector; $\vec{w}$ represents a white noise vector; $B_g$ is gyro bias; $B_a$ is accelerometer bias; ω is angular rate; subscripts 1-3 indicate sensor axes nominally aligned with roll, pitch, and yaw respectively; $\omega_a$ and $\omega_g$ are the break frequencies of the Markov processes for accelerometer and gyro biases, respectively; $B_{gn}$ and $B_{an}$ are gyro and accelerometer biases, respectively; $\omega_n$ is the angular rate generator, and $\omega_\theta$ is the break frequency of tilt input. In an exemplary embodiment, $B_g$=0.0024 rad/s rms with 0.006282 rad/s break frequency; $B_a$=0.012 m/s$^2$ rms with 0.006283 rad/s break frequency; ω=0.18 rad/s rms with 12.56 rad/s break frequency; $\omega_g=\omega_a$=0.006283 rad/s, $B_{gn}$=0.043 rad/s/√Hz double sided; $B_{an}$=0.22 m/s$^2$/√Hz double sided; $\omega_n$=0.07 rad/s/√Hz, and $\omega_\theta$=12.56 rad/s.

When the bias and angular rate thus generated are passed through their associated transfer functions, the states' rms biases result. In what follows, both the measurement and input noise are assumed to be zero mean. This assumption may be relaxed using standard techniques.

From equation (14), the quaternion propagation leads to the following four nonlinear first order differential equations:

$$\dot{q}_1 = -\frac{1}{2}(\omega_1 q_2 + \omega_2 q_3 + \omega_3 q_4) \quad (65)$$

$$\dot{q}_2 = \frac{1}{2}(\omega_1 q_1 - \omega_2 q_4 + \omega_3 q_3) \quad (66)$$

$$\dot{q}_3 = \frac{1}{2}(\omega_1 q_4 + \omega_2 q_1 - \omega_3 q_2) \quad (67)$$

$$\dot{q}_4 = \frac{1}{2}(-\omega_1 q_3 + \omega_2 q_2 + \omega_3 q_1) \quad (68)$$

where [$q_1$, $q_2$, $q_3$, $q_4$] is the quaternion defining rotation between body and local coordinates. The complete 13-state vector is given by:

$$\vec{x} = [\, \vec{x}_{1-9}^T \;\; q_1 \;\; q_2 \;\; q_3 \;\; q_4 \,]^T \quad (69)$$

The gyro outputs are linearly related to the input rate and gyro bias by:

$$\vec{y}_g = \begin{bmatrix} V_{g1} \\ V_{g2} \\ V_{g3} \end{bmatrix} = [\, I_{3\times3} \;\; O_{3\times3} \;\; I_{3\times3} \;\; O_{3\times4} \,]\vec{x} + \begin{bmatrix} V_{gn1} \\ V_{gn2} \\ V_{gn3} \end{bmatrix}, \quad (70)$$

where $V_g$ is the gyro output (measured in rad/s), $V_{gn}$ is gyro additive white noise, I is the identity matrix, and O is the zero matrix. In an exemplary embodiment, $V_{gn}$=6.8×10$^{-4}$ rad/s/√Hz double sided=140°/h/√Hz double sided.

The accelerometer outputs are linearly related to the accelerometer bias and are nonlinear in the quaternions that transform gravity into body coordinates. The unwanted high frequency subject accelerations are represented by additive white noise. Additional states could more flexibly represent high frequency accelerations.

The accelerometer outputs are linearly related to the input rate and accelerometer bias by:

$$\vec{y}_a = \begin{bmatrix} V_{a1} \\ V_{a2} \\ V_{a3} \end{bmatrix} = [\,0_{3\times3} \quad I_{3\times3} \quad 0_{3\times7}\,]\vec{x} + g\begin{bmatrix} 2(-q_1q_3 + q_2q_4) \\ 2(q_1q_2 + q_3q_4) \\ q_1^2 - q_2^2 - q_3^2 + q_4^2 \end{bmatrix} + \begin{bmatrix} V_{an1} \\ V_{an2} \\ V_{an3} \end{bmatrix}, \tag{71}$$

where g=−9.81 m/s$^2$, $V_a$ is accelerometer output (measured in m/s$^2$), and $V_{an}$ is accelerometer noise. In an exemplary embodiment, $V_{an}$=0.069 m/s$^2$/√Hz double sided.

The gyro noise is typically that of a commercial gyro, while the accelerometer noise is selected to yield accelerometer frequencies near 0.03 Hz as used in the complementary filters. Both the measurement and input noise are assumed to be zero mean, with the measurement noise not correlated to the input noise. These assumptions can be relaxed according to known techniques.

The combined output vector is defined by:

$$\vec{y} = \begin{bmatrix} \vec{y}_g \\ \vec{y}_a \end{bmatrix}. \tag{72}$$

For what follows, it is convenient to convert the continuous linear model described above to the discrete domain. In an exemplary embodiment, this is done by assuming a 0.01 s sampling interval, $T_s$, and that other inputs are constant across the sampling interval. The zero order hold (ZOH) assumption is also made, as described in K. Ogata, "Modern Control Engineering", Prentice-Hall, Englewood Cliffs, N.J., 1970. For the stochastic inputs, the power spectral densities of the continuous case are transformed to covariance by integrating the white noise power spectral densities (PSDs) from minus Nyquist to Nyquist frequency. In an exemplary embodiment, the Nyquist frequency is $0.5/T_s$. Thus $$Q_n = E[\vec{w}\vec{w}^T] = \begin{bmatrix} 0.188(r/s)^2 I_{3\times3} & 0_{3\times3} & 0_{3\times3} \\ 0_{3\times3} & 4.80(m/s^2)^2 I_{3\times3} & 0_{3\times3} \\ 0_{3\times3} & 0_{3\times3} & 0.49(r/s))^2 I_{3\times3} \end{bmatrix} \tag{73}$$

$$R_n = E[\vec{v}\vec{v}^T] = \begin{bmatrix} 4.70\times10^{-5}(r/s)^2 I_{3\times3} & 0_{3\times3} \\ 0_{3\times3} & 0.480(m/s^2)^2 I_{3\times3} \end{bmatrix} \tag{74}$$

where E[ ] is the expected value operator, $Q_n$ is the discrete covariance of the inputs (64) at time step n, and $R_n$ is the discrete covariance of outputs (70-72) at time step n. Again, inputs 1-3 correspond to gyros, and inputs 4-6 correspond to accelerometers.

Because the noise is separate from the nonlinear dynamics in the equations of motion and the output equation, we can employ the extended Kalman filter, in which the states are propagated between measurements by the continuous equations and the states are updated by measurements at discrete times. See A. Gelb, ed. "Applied Optimal Estimation", M.I.T. Press, Cambridge, Mass. 1974 ("Gelb"). We treat the initial covariance of the states as known. In practice, such initial covariance can be readily determined.

Generally, the Kalman filter will cycle between two phases: prediction and correction. During the prediction phase, the Kalman filter will predict the subject's state at the time of the next measurement, based on the subject's previously corrected state. In the correction phase, the Kalman filter will account for differences between the subject's predicted state and the subject's actual state, as determined from the measurement.

Between measurements, the subject's state at the time of the next measurement is predicted by a state predictor 82, and the covariance at that time is predicted by a covariance predictor 83. The predictors 82, 83 calculate a new state and covariance, respectively, according to the formulas $$\frac{d\hat{\vec{x}}}{dt} = f[\hat{\vec{x}}] \tag{75}$$

$$P_{k+1} = A_z\left[\hat{\vec{x}}_k(+)\right]Z_k A_z^T\left[\hat{\vec{x}}_k(+)\right] + B_z Q_n B_z^T \tag{76}$$

where the nonlinear function $f$, which is obtained from equations (60)-(69), describes the predictor 82, and where the predictor 83 produces $P_{k+1}$ as the predicted covariance based on an old covariance $Z_k$. The numerical integration starts with initial conditions $\vec{x}_k(+)$ and ends at $\vec{x}_{k+1}(-)$. The matrices A and B are calculated by linearizing equations (53)-(62). The ZOH discrete matrices $A_z$ and $B_z$ are recalculated at each step, periodically, or when the state estimates exceed certain value. In integrating the nonlinear function $f$ in equation (75), zero mean noise inputs are omitted.

After the measurement, which reads the sensor voltage 81 and corrects for instrument drift, misalignment, and other errors described above, the predicted state estimate is corrected by a state corrector 84. The corrector 84 is implemented by the formula:

$$\vec{x}_k(+) = \vec{x}_k(-) + M_k\{y_k - H[\vec{x}_k(-)]\}. \tag{77}$$

The nonlinear function H is obtained from equations 70-72. The matrix $M_k$ is called the innovation matrix. Generally, the innovation matrix accounts for differences between the predicted state and the measured state. With each measurement, the innovation matrix is recalculated by an innovation matrix updater 85 that is implemented by the formula $$M_k = P_k H^T[\vec{x}_k(-)]\{H[\vec{x}_k(-)]P_k H^T[\vec{x}_k(-)] + R\}^{-1}. \tag{78}$$

The covariance is corrected after the measurement by a covariance corrector 86. The corrected covariance $Z_k$ is determined from the formula:

$$Z_k = \left\{I - M_k C\left[\hat{\vec{x}}_k(-)\right]\right\}P_k, \tag{79}$$

where $$P_k = \left[\left(\vec{x}_k - \hat{\vec{x}}_k(-)\right)\left(\vec{x}_k - \hat{\vec{x}}_k(-)\right)^T\right]$$

= previously predicted covariance, and $$Z_k = E\left[\left(\vec{x}_k - \hat{\vec{x}}_k(+)\right)\left(\vec{x}_k - \hat{\vec{x}}_k(+)\right)^T\right]$$

= corrected covariance.

Fall Detection and Remediation

Any of the multi-axis, large angle vertical detection algorithms (Euler angles, quaternions, redundant Euler angles, or Kalman filter) estimate the elevation angle φ and the azimuth angle θ. The azimuth indicates the direction toward which the subject's head should move for the subject to attain vertical.

The elevation is restricted to 0 to $\pi$ radians, and indicates how far the subject has moved from vertical. For a given elevation angle, if the elevation angle is changing faster than a certain threshold, one would expect that the risk of a fall is heightened. If the elevation angle is beyond a different threshold, one would expect a fall is imminent. In either case, it is useful to trigger remedial action.

Figure 9:
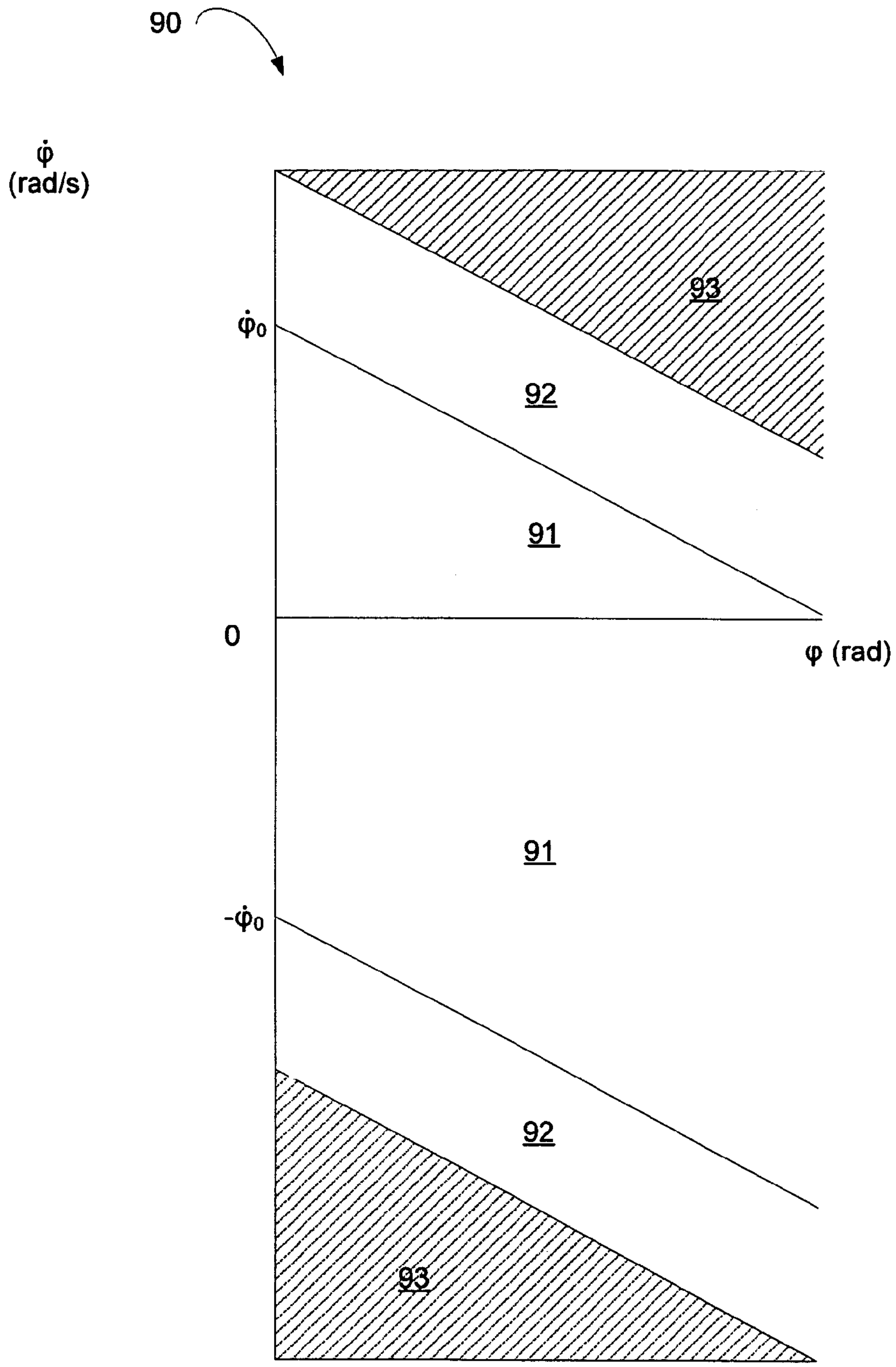
FIG. 9 is an exemplary decision space for fall detection and remediation.

An exemplary decision space 90, depicted for example in FIG. 9, is used to determine when to trigger remedial action, and what type of action is called for. When the subject has a particular elevation which is changing at an acceptably low rate, the subject is within the "safe zone" 91 and no remedial action is triggered. For example, in FIG. 9, for an upright subject (angle of elevation=0), the subject's elevation may change at a rate less than $|\dot{\phi}_0|$ and remain in the safe zone. For motion beyond this range, the subject is outside the safe zone, and remedial action will be taken. For non-zero elevation, a negative rate larger than the positive rate may be permissible, since, a negative rate would indicate that the subject is moving toward the vertical.

The decision space may be partitioned into several regions, one of which being the safe zone 91. Other regions correspond to different remedial actions. For example, region 92 may be chosen to reflect situations in which the subject bears a heightened (but not imminent) risk of falling. In this case, remedial action such as sounding an alarm or providing additional stimulus to the subject may be taken. Region 93 may be chosen to reflect situations in which a fall is imminent. In this case, remedial action intended to mitigate the adverse effects of the fall may be taken. For example, the prosthesis may: deploy an airbag or initiate an automated call for help.

Accordingly, other embodiments are within the scope of the following claims.

What is claimed is:

1. A vestibular prosthesis comprising:

a wearable motion sensing system including accelerometers and gyroscopes, the motion sensing system is configured to generate motion signals indicative of a motion thereof, wherein the motion includes rotation about two distinct axes;

a signal processor in communication with the motion sensing system, the signal processor being configured to generate a first estimate of a tilt of the motion sensing system based on a nonlinear relationship between output from the accelerometers and quaternions that transform a direction of a gravity vector into a body frame of reference that is stationary with respect to the motion sensing system, to generate a second estimate of the tilt based on output from the gyroscopes, to generate a third estimate of the tilt based on the first estimate and the second estimate, and to represent the first, second, and third estimates as quaternions;

an actuator configured to be triggered responsive to the third estimate of the tilt being in a predetermined region of a decision space having a first dimension representing a value of the tilt and a second dimension representing a rate of change of the tilt.

2. The prosthesis of claim 1, further comprising a stimulator in communication with the actuator, the stimulator being configured to generate a stimulus signal based on the tilt of the motion sensing system.

3. The prosthesis of claim 1, wherein the signal processor is configured to generate the third estimate by using a Kalman filter.

4. The prosthesis of claim 1, further comprising an airbag in communication with the actuator, wherein the signal processor is configured to cause the actuator to deploy the airbag when the tilt of the motion sensing system is within a the pre-determined region of the decision space, or when the motion has pre-determined characteristics.

5. The prosthesis of claim 1 wherein the signal processor is configured to reject errors caused by low-frequency drift of the gyroscopes and high-frequency acceleration of the accelerometers.

6. The prosthesis of claim 1 wherein a range of the tilt includes 0 degrees and 180 degrees.

7. The prosthesis of claim 1 wherein the actuator is configured to deliver a signal selected from the group consisting of: a tactile signal delivered by vibrating elements, an acoustic signal delivered by a headset, a visual signal delivered by selectively illuminated light sources, and a deployment signal for deploying an airbag.

8. A vestibular prosthesis comprising:

a wearable motion sensing system including accelerometers and gyroscopes, the motion sensing system is configured to generate motion signals indicative of a motion thereof, wherein the motion includes rotation about two distinct axes;

a signal processor in communication with the motion sensing system, the signal processor being configured to generate a first estimate of a tilt of the motion sensing system based on a direction of a gravity vector, in a body frame of reference that is stationary with respect to the motion sensing system, determined based on Euler angles relating a motion of the accelerometers to the tilt of the motion sensing system, to generate a second estimate of the tilt based on Euler angles relating motion of the gyroscopes to the tilt of the motion sensing system, and to generate a third estimate of the tilt based on the first estimate and the second estimate, and an actuator configured to be triggered responsive to the third estimate of the tilt being in a predetermined region of a decision space having a first dimension representing a value of the tilt and a second dimension representing a rate of change of the tilt.

9. The prosthesis of claim 8, wherein the signal processor is configured to determine a first redundant Euler angle and a second redundant Euler angle, and generate the first estimate based further on the first redundant Euler angle, and generate the second estimate based on the second redundant Euler angle.

10. The prosthesis of claim 8, further comprising a stimulator in communication with the actuator, the stimulator being configured to generate a stimulus signal based on the tilt of the motion sensing system.

11. The prosthesis of claim 8, further comprising an airbag in communication with the actuator, wherein the signal processor is configured to cause the actuator to deploy the airbag when the tilt of the motion sensing system is within a predetermined range, or when the motion has pre-determined characteristics.

12. The prosthesis of claim 8, wherein the signal processor is configured to generate the third estimate by using a Kalman filter.

13. The prosthesis of claim 8 wherein the signal processor is configured to reject errors caused by low-frequency drift of the gyroscopes and high-frequency acceleration of the accelerometers.

14. The prosthesis of claim 8 wherein a range of the tilt includes 0 degrees and 180 degrees.

15. The prosthesis of claim 8 wherein the actuator is configured to deliver a signal selected from the group consisting of: a tactile signal delivered by vibrating elements, an acoustic signal delivered by a headset, a visual signal delivered by selectively illuminated light sources, and a deployment signal for deploying an airbag.

16. A method of estimating a tilt of a wearer, the method comprising:

generating, by a motion sensor, motion signals indicative of rotations about at least two axes as experienced by the wearer, wherein generating the motion signals includes generating accelerometer signals and gyro signals, processing the accelerometer signals including determining an accelerometer quaternion, and processing the gyro signals including determining a gyro quaternion;

generating, by a processor, a first estimate of the tilt of the wearer based on a nonlinear relationship between the accelerometer signals and quaternions that transform a direction of gravity into a body frame of reference that is stationary with respect to the motion sensing system;

generating, by the processor, a second estimate of the tilt of the wearer based on the gyro signals;

generating, by the processor, a third estimate of the tilt of the wearer based on the first and second estimates; and providing an output signal to a nervous system of the wearer, the output signal being indicative of the third estimate of the tilt of the wearer and responsive to determining that the third estimate is in a predetermined region of a decision space having a first dimension representing the value of the tilt and a second dimension representing a rate of change of the tilt.

17. The method of claim 16 further comprising taking remedial action in response to determining that the third estimate of the tilt of the wearer is in the predetermined region of the decision space.

18. The method of claim 17, wherein taking remedial action comprises deploying an airbag worn by the wearer.

19. The method of claim 17 further comprising monitoring changing values of the third estimate with respect to the decision space.

20. The method of claim 17 wherein the predetermined region includes:

at least a first region in which no remedial action is triggered, at least a second region in which a first remedial action is triggered, and at least a third region in which a second remedial action different from the first remedial action is triggered.

21. The method of claim 16, wherein generating the third estimate includes combining the first and second estimates by using a Kalman filter.

22. A method of estimating a tilt of a wearer, the method comprising:

generating, by a motion sensor, motion signals indicative of rotations about at least two axes as experienced by the wearer, wherein generating the motion signals includes generating accelerometer signals and gyro signals, processing the accelerometer signals including determining accelerometer Euler angles, and processing the gyro signals including determining gyro Euler angles;

generating, by a processor, a first estimate of the tilt of the wearer based on a direction of a gravity vector, in a body frame of reference that is stationary with respect to the motion sensing system, determined based on the accelerometer Euler angles determined from processing the accelerometer signals;

generating, by the processor, a second estimate of the tilt of the wearer based on the gyro signals;

generating, by the processor, a third estimate of the tilt of the wearer based on the first and second estimates; and providing an output signal to a nervous system of the wearer, the output signal being indicative of the third estimate of the tilt of the wearer and responsive to determining that the third estimate is in a predetermined region of a decision space having a first dimension representing the value of the tilt and a second dimension representing a rate of change of the tilt.

23. The method of claim 22, further comprising taking remedial action in response to determining that the third estimate of the tilt of the wearer is in the predetermined region of the decision space.

24. The method of claim 23 further comprising monitoring changing values of the third estimate with respect to the decision space.

25. The method of claim 23 wherein the predetermined region includes:

at least a first region in which no remedial action is triggered, at least a second region in which a first remedial action is triggered, and at least a third region in which a second remedial action different from the first remedial action is triggered.

26. The method of claim 23, wherein taking remedial action comprises deploying an airbag worn by the wearer.

27. The method of claim 22, wherein processing the accelerometer signals further includes determining a first redundant Euler angle, and processing the gyro signals further includes determining a second redundant Euler angle.

28. The method of claim 22, wherein generating the third estimate includes combining the first and second estimates.

* * * * *

UNITED STATES PATENT AND TRADEMARK OFFICE

CERTIFICATE OF CORRECTION

PATENT NO. : 8,092,398 B2
APPLICATION NO. : 11/401106
DATED : January 10, 2012
INVENTOR(S) : Marc S. Weinberg It is certified that error appears in the above-identified patent and that said Letters Patent is hereby corrected as shown below:

Col. 26, delete “a the” (line 4) and insert -- the --, therefor.

Signed and Sealed this
Twenty-eighth Day of February, 2012

David J. Kappos
*Director of the United States Patent and Trademark Office*